US 6,503,632 B1
United States Patent
Hayashi et al.

(10) Patent No.: US 6,503,632 B1
(45) Date of Patent: Jan. 7, 2003

(54) POLYDIALKYLSILOXANE/POLYAMIDE COPOLYMER, PROCESS FOR PRODUCING THE SAME, AND VARIOUS MATERIALS

(75) Inventors: Akio Hayashi, Tokyo (JP); Daijiro Shiino, Sayama (JP); Mitsuru Akashi, Kagoshima (JP); Ryuzo Hosotani, Nishinomiya (JP); Kensaku Sonoda, Tsukuba (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 09/762,962

(22) PCT Filed: Aug. 13, 1999

(86) PCT No.: PCT/JP99/04388

§ 371 (c)(1),
(2), (4) Date: Feb. 14, 2001

(87) PCT Pub. No.: WO00/09587

PCT Pub. Date: Feb. 24, 2000

(30) Foreign Application Priority Data

Aug. 14, 1998 (JP) .............................................. 10-229629

(51) Int. Cl.[7] .......................... B32B 9/04; B32B 27/34; C08L 83/10; C08L 77/00
(52) U.S. Cl. ..................... 428/447; 428/474.4; 525/431
(58) Field of Search ................................. 525/431, 420; 428/447, 474.4, 448

(56) References Cited

FOREIGN PATENT DOCUMENTS

| JP | 62-223228 |   | 10/1987 |           |
|----|-----------|---|---------|-----------|
| JP | 01123824  | * | 5/1989  | C08G/69/42 |
| JP | 01219718  | * | 9/1989  | C08G/69/32 |
| JP | 02-269122 |   | 11/1990 |           |
| JP | 08-059826 |   | 3/1996  |           |

* cited by examiner

Primary Examiner—Robert Dawson
Assistant Examiner—Michael J Feely
(74) Attorney, Agent, or Firm—Darby & Darby

(57) ABSTRACT

A novel polydialkylsiloxane/polyamide copolymer which is excellent in biocompatibility, mechanical strength, and heat moldability, applicable for use in medical materials, ophthalmic materials, cosmetics, and electronic materials, and has a main chain represented by the formula (4), one end represented by the formula (5) and another end represented by the formula (6):

—(NH—A—NHCO—B—CO)$_m$—     (4)

—NH—A—NH—X$^2$             (5)

—X$^1$                      (6)

wherein the ratio of —R$^1$—(Si(R$^2$) (R$^3$)—O)n$^1$-Si(R$^2$) (R$^3$)—R$^1$— as A to the divalent organic group having 1 to 20 carbon atoms as A is within the range of 1:0.01~100, and the proportion of X$^1$ and X$^2$ being hydrogen atoms is 10% or less relative to all the end groups, a process for producing the same, and a variety of its uses.

39 Claims, 7 Drawing Sheets

POLYDIALKYLSILOXANE/POLYAMIDE COPOLYMER, PROCESS FOR PRODUCING THE SAME, AND VARIOUS MATERIALS

This is a National Stage application of PCT/JP99/04388, filed Aug. 13, 1999, now WO 00/09587, published Mar. 24, 2000, which claim priority to Japanese Application No. H10-229629, filed Aug, 14, 1998.

TECHNICAL FIELD

The present invention relates to a novel polydialkylsiloxane/polyamide copolymer, a process for producing the same, and to various materials such as ophthalmic materials such as contact lenses and intraocular lenses, medical materials such as antithrombotic materials, and a variety of cosmetic compositions or electronic materials formed with the copolymer.

BACKGROUND ART

Siloxane polymers typified by polydimethylsiloxane have excellent biocompatibility, gas permeability, and other functions, and their various uses in the medical field have been awaited, some of which have been brought into practice. However, conventional siloxane polymers have a problem in strength and therefore their uses are limited.

Under the circumstances, polymers having both an alkylamide group excellent in strength, particularly an aramid segment such as an aromatic polyamide (aramid), and a siloxane segment excellent in biocompatibility and the like are now under development.

For example, there has been proposed a complexed polymer formed by copolymerizing a siloxane polymer with aramid (Japanese Patent Application Laid-Open No. Hei 1-12384), and there have been disclosed that this polymer serves as an excellent biocompatible material (Japanese Patent Application Laid-Open No. Hei 2-203863 and Japanese Patent Application Laid-Open No. Hei 5-285216) and that this polymer can be utilized as a contact lens material (Japanese Patent Application Laid-Open No. Hei 6-313864).

According to the production method of the siloxane/aramid copolymers, such copolymers appear to be a material in which at least dozens of percentages of free amino groups remain at its ends. Moreover, since the aramid segment of the siloxane/aramid copolymer dissolves in a limited variety of solvent systems, the biocompatibility test which is carried out on each of these copolymers provides nothing but the evaluation results of the film molded therefrom according to the solvent casting method in which a solvent such as N,N-dimethylacetamide (hereinafter, abbreviated as DMAc), dimethylformamide (hereinafter, abbreviated as DMF), or the like is employed.

Generally, a molded article obtained according to the solvent casting method is made almost free from solvent by being subjected to a solvent-removing treatment comprised of heating the article to the glass transition temperature of the polymer or higher and lowering the pressure. However, when a solvent like DMF or DMAc having a high polarity and a relatively high boiling point is employed, removing the solvent to such an extent as is considered to be non-problematic in terms of the use as a medical material is extremely difficult. Therefore, for use as a medical material, it would be desirable that a copolymer is heat-moldable without using a solvent, and the copolymer is required to have a sufficient thermal stability.

However, the heretofore suggested complexed polydialkylsiloxane/polyamide copolymer formed by block-copolymerizing a siloxane polymer with aramid has a problem that, when heated to a certain temperature to evaporate the solvent completely or examine its fluidity upon heating after having been molded by the solvent casting method, it turns pale yellow and further browns. In addition, there is a problem that, due to crosslinking reaction, an attempt to dissolve the heat-dried copolymer in the same solvent again will result in failure. Furthermore, it has come to be known that there is a problem that heating the copolymer to high temperatures causes its liquid siloxane component to decompose and elute. Therefore, when heat-molding such polymer, sufficient care must be taken over the temperature control, heating time and the like. Further, such polymer is inapplicable to ophthalmic or medical materials, for not only is such polymer difficult to heat-mold, but also heat treatment for removing the solvent inevitably incorporated therein is arduous.

Surface and Interface Analysis, Vol. 10, p416–423 (1987) and Surface and Interface Analysis, Vol. 13, p233–236 (1998) report that plasma irradiation is carried out to render the surface of a contact lens made of an acrylate polymer having a siloxane side chain hydrophilic. Polymer Journal, Vol. 42, p841–847 (1985) also reports that a silicone rubber contact lens is subjected to plasma irradiation thereby to make its surface hydrophilic. However, there exists a problem that, even after such treatment, it is difficult for the lens to retain its hydrophilicity over a long period of time and that adhesion of protein onto the lens surface becomes considerable.

In Polymer Journal, Vol. 20, p485–491 (1988), it is reported that, as can be understood from the fact that the gas permeability of polydimethylsiloxane is not adversely affected even if it is subjected to electron beam irradiation at a dose of 80 Mrad, electron beam irradiation at a dose of 80 Mrad or so does not cause neither crosslinking nor decomposition in the chemical structure. On the other hand, in Adhesion, Vol. 34 p201–209 (1991), it is reported that, as a result of the swellability (solubility) test made on polydimethylsiloxane irradiated with an electron beam, polydimethylsiloxane was completely dissolved at 20 KGy (=2 Mrad) or less and that crosslinking was observed at 50 KGy (=5 Mrad) or more. The publication also says that such electron beam irradiation raises the storage modulus (G') and loss modulus (G").

These publications referred only to energy beam irradiation of siloxane polymers, and none of them touched on improvements in physical properties resulting from energy beam irradiation of a molded article of the polydialkylsiloxane/polyamide copolymer.

The above-mentioned polydialkylsiloxane/polyamide copolymer is what is constituted of siloxane chains into which, mainly for supplementing strength-related drawbacks of a siloxane polymer, aramid segments have been introduced as multi blocks. As compared to a molded article which is exclusively made of a siloxane polymer, its molded article fabricated by the solvent casting or heat-molding method has a largely improved strength as it is, which is due to the interaction between the aramid segments. However, with respect to the influence the aramid segment to siloxane segment ratio of the polydialkylsiloxane/polyamide copolymer exerts, its strength owing to aramid and such functions as oxygen permeability and biocompatibility due to siloxane are in a trade-off relation. Therefore, when aiming. for a still higher, well-balanced performance, its physical properties need to be improved not by varying the ratio but by other means.

A polyamide, due to its amide bonding, shows relatively good hydrophilicity. However, it has been known that, when a polyamide is complexed with a siloxane-type polymer as in the case of a polydialkylsiloxane/polyamide copolymer, the resulting material will be highly hydrophobic, which is because the mobility of its siloxane segments at the molecular level is good and thus the surface of the material is covered by the siloxane segments. Although not all the medical materials are required to be hydrophilic and whether hydrophilicity is a requisite or not depends on the intended use, for example, contact lens materials need to be hydrophilic in view of not only a good fit to the eye but also the prevention of a lens from, as a result of a long-time wear, clinging to the cornea of the eyeball. To give an example, silicone elastomer contact lenses have once been put into practical use, which resulted in failure because their hydrophilicity was insufficient.

Thus, for expanding the uses of a molded article of a highly hydrophobic polydialkylsiloxane/polyamide copolymer, it is necessary to impart hydrophilicity to the surface thereof. However, nothing has been heretofore proposed to improve the hydrophilicity of polydialkylsiloxane/polyamide copolymer molded articles.

On the contrary, copolymers having a phosphorylcholine derivative group have been studied from various aspect because of their excellent contamination resistance, hydrophilicity, and biocompatibility. For example, there have been known a process for providing a copolymer by copolymerizing a monomer having a phosphorylcholine derivative group, a process comprising coating a copolymer having the above-mentioned functional group onto a substrate, and a process comprising chemically bonding a copolymer having the aforementioned functional group to a material having a reactive group (Japanese Patent Application Laid-Open No. Hei 3-39309, Japanese Patent Publication No. Hei 6-502200, Japanese Patent Application Laid-Open No. Hei 5-70321, Patent No. 2593993, Japanese Patent Application Laid-Open No. Hei 9-3132, Japanese Patent Publication No. Hei 7-502053, Japanese Patent Application Laid-Open No. Hei 5-1177119, Japanese Patent Application Laid-Open No. Hei 4-283653, "Y. Iwasaki, K. Ishihara, N. Nakabayashi, C. Khang, J. H. Jeon, J. W. Lee, and H. B. Lee, J. Biomater. Sci., Polym, Edn., 9(8), p801–816 (1998)").

However, that it is possible to bond a copolymer having the aforementioned functional group to a polydialkylsiloxane/polyamide copolymer chemically by coating the latter on the former is not known.

Further, in the synthesis of a polydialkylsiloxane/polyamide copolymer, solvents such as pyridine, ethers such as dioxane and tetrahydrofuran and dimethylformamide are the only solvents that have been proposed for the case of the use of a dicarboxylic compound and a diamino compound as starting materials (Japanese Patent Application Laid-Open No. Hei 6-329791, Japanese Patent Publication No. Hei 1-23490, Japanese Patent Application Laid-Open No. Hei 7-292342). Chloroform is the only heretofore proposed example of a solvent for use in the case where a dicarboxylic acid chloride and a diamino compound are employed as starting materials (Japanese Patent Publication No. Hei 1-23490, Japanese Patent Application Laid-Open No. Hei 1-123824, Patent No. 2743432, Japanese Patent Application Laid-Open No. Hei 6-313864, Japanese Patent Application Laid-Open No. Hei 5-285216, Japanese Patent Application Laid-Open No. Hei 7-292342, Japanese Patent Application Laid-Open No. Hei 11-80360).

An intraocular lens, an example of the ophthalmic material, is a substitute for a crystalline lens which, for a variety of causes, suffers from cataract and became turbid. Recent operations for cataract have undergone improvements, utilizing the combination of phacoemulsification through a small incision and an intraocular lens made of a soft material.

By the way, intraocular lenses each constituted of a soft optical member and a plurality of fixation members for holding the optical member include three-piece ones and one-piece ones, and they are classified according to how the optical member and the fixation members, which are made from different materials, are connected. Further, in recent years, an intraocular lens being the integrally molded article of an optical member and fixation members, a so-called plate lens, has become known.

Unlike in the case of a conventional hard lens made of PMMA, a flexible lens cannot be subject to mechanical processing such as cutting or grind, because of softness of the material. Therefore, the optical member is made by the cast mold method in which an optical member molding material being for example a monomer, prepolymer, or oligomer is polymerized within a mold. Moreover, there is a problem that, when attaching the fixation members to the optical member, a technique other than conventional ones must be employed because it is also impossible to make pores in the optical member mechanically.

DISCLOSURE OF THE INVENTION

It is an object of the present invention to provide a novel polydialkylsiloxane/polyamide copolymer which is excellent in biocompatibility, mechanical strength, and thermal moldability and usable in a wide range of medical, ophthalmic, cosmetic, or electronic materials, and a process for producing the same.

It is another object of the present invention to provide a molded article which is excellent in biocompatibility, mechanical strength, and thermal moldability, substantially free from a solvent inevitably incorporated therein in the course of production, capable of keeping its transparency, and usable in a wide variety of medical, ophthalmic, cosmetic, or electronic materials.

It is another object of the present invention to provide an ophthalmic material such as contact lenses and intraocular lenses or a medical material such as antithrombotic materials which is excellent in biocompatibility, mechanical strength, thermal moldability, and hydrophilicity, substantially free from a solvent inevitably incorporated therein in the course of production, and capable of keeping its transparency.

It is still another object of the present invention to provide a cosmetic composition which, when applied onto the skin, shows excellent water resistance, oil resistance, durability, and ultraviolet ray blocking properties, has an excellent capability of keeping the shape of for example hair, and is usable in a variety of cosmetic products.

It is still another object of the present invention to provide an electronic material which is excellent in optical characteristics such as transparency, thermal moldability, and mechanical properties, shows insulation performance, and is usable in the electric, electronic, and optical device fields.

The inventors of the present invention made intensive studies to achieve the above-mentioned objects, and finally found that a novel polydialkylsiloxane/polyamide copolymer possessing excellent biocompatibility and high-level gas permeability together with high mechanical strength wherein such a reaction as crosslinking or decomposition which is caused under chemical, thermal, or mechanical stress with its amino, carboxylic acid chloride, or carboxylic acid group as an active site is inhibited from occurring. The copolymer can be obtained by reacting a siloxane oligomer having amino groups at both ends, an aromatic diamino compound, an aliphatic diamino compound, and an aromatic dicarboxylic acid chloride or aliphatic dicarboxylic acid chloride in a suitable ratio and reaction order, acylating part or all of the amino groups remaining at ends of the resulting copolymer, and carrying out alkylamidation, or by reacting with a compound having a hydroxyl group and/or an amino group after the dicarboxylic acid chloride has been reacted. The present invention was completed based on this finding.

Moreover, they also found that a copolymer of high transparency and excellent thermal moldability can be obtained through the use of, as a polymerization solvent to be employed in the synthesis of a polydialkylsiloxane/polyamide copolymer, a solvent selected from the group consisting of dimethylformamide, dimethylacetamide, tetrahydrofuran, dioxane, diglyme, acetonitrile, dimethoxyethane, acetone, methyl ethyl ketone, methyl acetate, ethyl acetate, and a mixture thereof. The present invention was completed based on this finding.

Further, they found that a molded article made of this novel polydialkylsiloxane/polyamide copolymer is stable against mechanical stress, has an enhanced stability against deterioration with time, and is largely improved in color change resistance and anti-degradation properties, and that it is easy to render this molded article hydrophilic. The molded article, ophthalmic material, medical material, and electronic material of the present invention were completed based on this findings.

Furthermore, the inventors found that cosmetics incorporating this novel polydialkylsiloxane/polyamide copolymer or its molded article show excellent water resistance, oil resistance, durability, and ultraviolet ray blocking properties and are effective in keeping the shape of for example hair. The cosmetic composition of the present invention was completed based on this finding.

According to the present invention, there is provided a polydialkylsiloxane/polyamide copolymer obtained by polymerizing an amino compound represented by the formula (1) and having amino groups at both ends and a dialkylsiloxane chain:

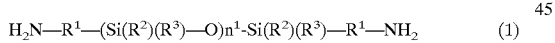
$H_2N—R^1—(Si(R^2)(R^3)—O)n^1-Si(R^2)(R^3)—R^1—NH_2$ (1)

wherein $R^1$ represents a divalent organic group having 1 to 10 carbon atoms, $R^2$ and $R^3$ are the same or different, each representing an organic group having 1 to 7 carbon atoms, and $n^1$ denotes an integer of 5 to 200, a diamino compound represented by the formula (2):

$H_2N—A^1—NH_2$ (2)

wherein $A^1$ represents a divalent organic group having 1 to 20 carbon atoms, and a dicarboxylic acid chloride represented by the formula (3):

$ClCO—B—COCl$ (3)

wherein B represents a divalent organic group having 1 to 20 carbon atoms to give a polydialkylsiloxane/polyamide copolymer (A) containing amino groups at the ends thereof in which the ratio of —$R^1$—$(Si(R^2)(R^3)$—O)$n^1$-Si($R^2$)($R^3$)—$R^1$— to —$A^1$— is within the range of 1:0.01~100, and reacting the copolymer (A) thus obtained with an acyl chloride having 2 to 8 carbon atoms.

Moreover, according to the present invention, there is provided a polydialkylsiloxane/polyamide copolymer obtained by polymerizing an amino compound represented by the formula (1) and having amino groups at both ends and a dialkylsiloxane chain, a diamino compound represented by the formula (2), and a dicarboxylic acid chloride represented by the formula (3) to give a polydialkylsiloxane/polyamide copolymer (A) containing amino groups at the ends thereof in which the ratio of —$R^1$—$(Si(R^2)(R^3)$—O)$n^1$-Si($R^2$)($R^3$)—$R^1$— to —$A^1$— is within the range of 1:0.01~100, reacting the copolymer (A) thus obtained with a dicarboxylic acid chloride represented by the formula (3), and then with a compound selected from the group consisting of a monovalent hydroxyl group-containing compound having 1 to 8 carbon atoms, a monovalent amino group-containing compound having 1 to 8 carbon atoms, and a mixture thereof.

Furthermore, according to the present invention, there is provided a polydialkylsiloxane/polyamide copolymer which has a main chain represented by the formula (4), one end represented by the formula (5) and another end represented by the formula (6):

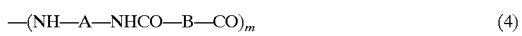
—(NH—A—NHCO—B—CO)$_m$— (4)

—NH—A—NH—$X^2$ (5)

—$X^1$ (6)

wherein $X^1$ and $X^2$ each represents —$COR^4$, —CO—B—$COR^5$ (where $R^4$ represents an organic group having 1 to 7 carbon atoms, $R^5$ represents hydroxyl group, —$OR^6$ or —$NHR^6$ (where $R^6$ represents an organic group having 1 to 7 carbon atoms) and B represents a divalent organic group having 1 to 20 carbon atoms) or hydrogen atom; A represents —$R^1$—$(Si(R^2)(R^3)$—O)$n^1$-Si($R^2$)($R^3$)—$R^1$— (where $R^1$ represents a divalent organic group having 1 to 10 carbon atoms, $R^2$ and $R^3$ are the same or different, each representing an organic group having 1 to 7 carbon atoms, and $n^1$ denotes an integer of 5 to 200) or a divalent organic group having 1 to 20 carbon atoms; B represents a divalent organic group having 1 to 20 carbon atoms; and m denotes an integer of 5 to 200, wherein the ratio of —$R^1$—$(Si(R^2)(R^3)$—O)$n^1$-Si($R^2$)($R^3$)—$R^1$— as A to the divalent organic group having 1 to 20 carbon atoms as A is within the range of 1:0.01~100, and the proportion of $X^1$ and $X^2$ being hydrogen atoms is 10% or less relative to all the end groups in the copolymer.

Further, according to the present invention, there is provided a process for producing the above-described polydialkylsiloxane/polyamide copolymer in which, after a copolymer (A) having a main chain represented by the formula (4), one end represented by the formula (5) and another end represented by the formula (6) in which the ratio of —$R^1$—$(Si(R^2)(R^3)$—O)$n^1$-Si($R^2$)($R^3$)—$R^1$— as A to a divalent organic group having 1 to 20 carbon atoms as A is within the range of 1:0.01 ~100 is obtained, the step (I) in which the copolymer (A) is reacted with an acyl chloride having 2 to 8 carbon atoms to alkylamidate hydrogen atoms represented by $X^1$ and $X^2$ in the copolymer (A) so that the proportion of $X^1$ and $X^2$ being hydrogen atoms is 10% or less relative to all the end groups in the resulting copolymer, or the step (II) in which the copolymer (A) is reacted with a dicarboxylic acid chloride represented by the formula (3), and then with a compound selected from the group consisting of a monovalent hydroxyl group-containing compound having 1 to 8 carbon atoms, a monovalent amino group-containing compound having 1 to 8 carbon atoms, and a mixture thereof so that, in the copolymer, the proportion of $X^1$ and $X^2$ being hydrogen atoms is 10% or less, is carried out.

Furthermore, according to the present invention, there is provided a molded article obtained by molding a molding material containing at least one kind of polydialkylsiloxane/polyamide copolymer described above.

The present invention further provides an ophthalmic or medical material comprising the above-described molded article.

The present invention further provides a cosmetic composition or electronic material containing at least either the polydialkylsiloxane/polyamide copolymer or the molded article.

BEST MODE FOR CARRYING OUT THE INVENTION

Figure 1:
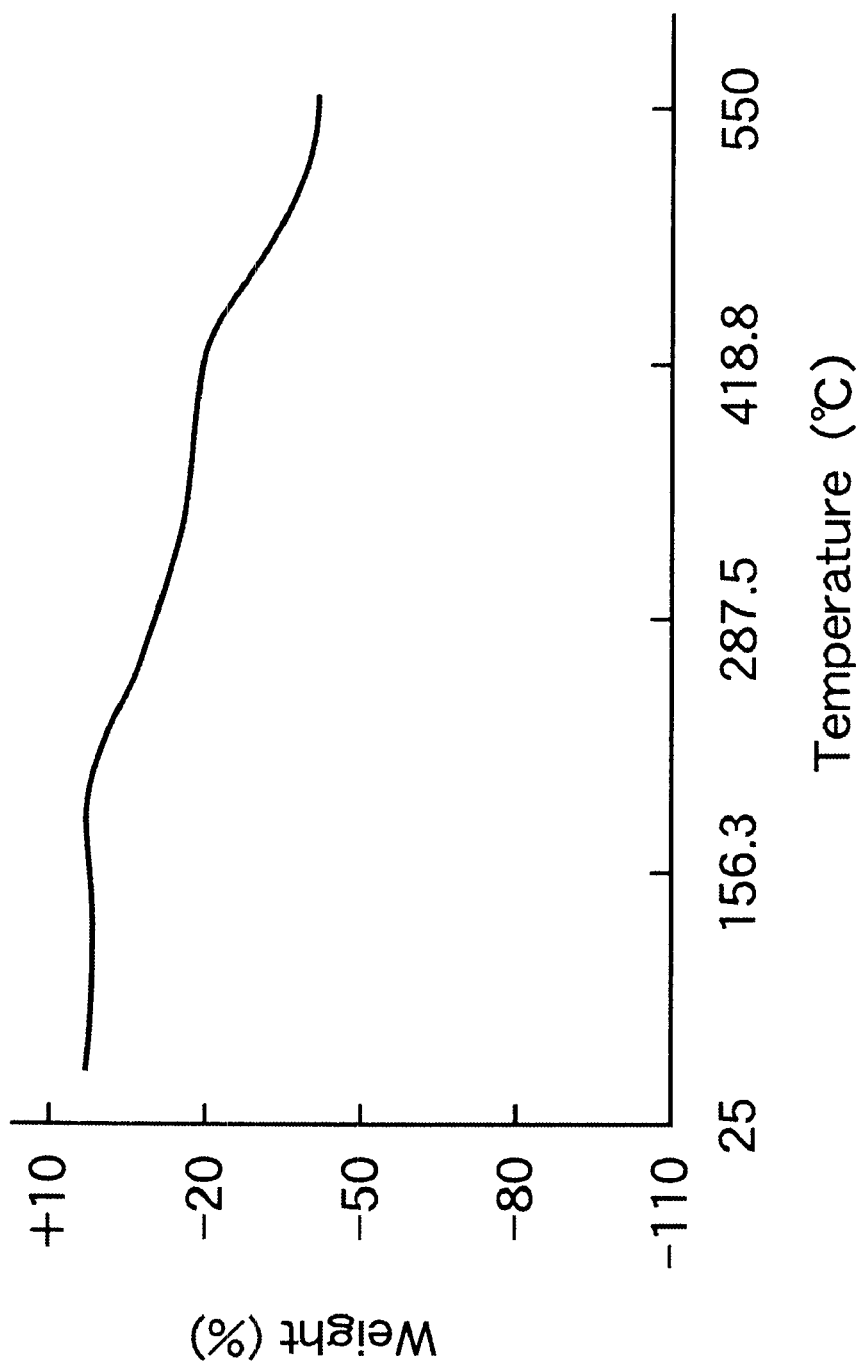
FIG. 1 is a graph showing the relation between the temperature and the weight loss (%) of the cast membrane obtained through the thermogravimetry of the p-17-70 cast membrane conducted in Example 8.

Hereinafter, the present invention will be described in further detail.

The polydialkylsiloxane/polyamide copolymer of the present invention (hereinafter, referred to as the copolymer of the present invention) is obtained by polymerizing an amino compound represented by the formula (1) and having amino groups at both ends and a dialkylsiloxane chain:

$$H_2N\text{—}R^1\text{—}(Si(R^2)(R^3)\text{—}O)n^1\text{-}Si(R^2)(R^3)\text{—}R^1\text{—}NH_2 \quad (1),$$

a diamino compound represented by the formula (2):

$$H_2N\text{—}A^1\text{—}NH_2 \quad (2),$$

and a dicarboxylic acid chloride represented by the formula (3):

$$ClCO\text{—}B\text{—}COCl \quad (3)$$

to give a polydialkylsiloxane/polyamide copolymer (A) containing amino groups at the ends thereof in which the ratio of —$R^1$—$(Si(R^2)(R^3)$—O$)n^1$-Si$(R^2)(R^3)$—$R^1$— to —$A^1$— is within the range of 1:0.01~100, and reacting the copolymer (A) thus obtained with an acyl chloride having 2 to 8 carbon atoms, or reacting the copolymer (A) with a dicarboxylic acid chloride represented by the formula (3) and then with a compound selected from the group consisting of a monovalent hydroxyl group-containing compound having 1 to 8 carbon atoms, a monovalent amino group-containing compound having 1 to 8 carbon atoms, and a mixture thereof. In either case, the resulting copolymers are similarly terminated. By allowing the copolymer (A) to react with a dicarboxylic acid chloride represented by the formula (3), there is provided a polydialkylsiloxane/polyamide copolymer terminated with acid chloride.

In the formula (1), $R^1$ represents a divalent organic group having 1 to 10 carbon atoms such as p-phenylene group, o-phenylene group, m-phenylene group, 4,4'-diphenyleneether group, 4,3'-diphenyleneether group, 4,4'-diphenylene group, 4,3'-diphenylene group, 4,4'-phenylenedimethylene group, 4,4'-thiodiphenylene group, 4,3'-thiodiphenylene group, 4,4'-propylenediphenylene group, 4,3'-propylenediphenylene group, 4,4'-methylenediphenylene group, and 4,3'-methylenediphenylene group. $R^2$ and $R^3$ are the same or different, each representing an organic group having 1 to 7 carbon atoms such as methyl group, ethyl group, phenyl group, hydroxyphenyl group, vinyl group, 3,3,3-trifluoropropyl group, (meth) acryloyloxyalkyl group, β-phenyl (meth)acryloyloxyalkyl group, azidobenzoyloxyalkyl group, and mercaptoalkyl group. Methyl, ethyl, phenyl, hydroxyphenyl, vinyl, 3,3,3-trifluoropropyl groups are preferred. $n^1$ denotes an integer of 5 to 200.

As the amino compound represented by the formula (1), oligomers expressed by the formulae listed below are preferable, and these can be used either singly or as a mixture. In the formulae, Ph represents phenyl group, and a and b each denotes an integer of 1 to 10.

$NH_2(CH_2)a\text{-}(Si(CH_3)_2O)n^1\text{-}Si(CH_3)_2\text{—}(CH_2)bNH_2$,
$NH_2(CH_2)a\text{-}(Si(C_2H_5)_2O)n^1\text{-}Si(C_2H_5)_2\text{—}(CH_2)bNH_2$,
$NH_2(CH_2)a\text{-}(Si(CH_3)(C_6H_5)O)n^1\text{-}Si(CH_3)(C_6H_5)\text{—}(CH_2)bNH_2$,
$NH_2(CH_2)a\text{-}(Si(C_6H_5)_2O)n^1\text{-}Si(C_6H_5)_2\text{—}(CH_2)bNH_2$,
$NH_2(CH_2)a\text{-}(Si(CH_3)(C_6H_4OH)O)n^1\text{-}Si(CH_3)(C_6H_4OH)\text{—}(CH_2)bNH_2$,
$NH_2(CH_2)a\text{-}(Si(CH_3)_2O)n^1\text{-}(Si(CH=CH_2)_2O)n^1\text{-}Si(CH_3)_2\text{—}(CH_2)bNH_2$,
$NH_2(CH_2)a\text{-}(Si(CH_3)(CH_2CH_2CF_3)O)n^1\text{-}Si(CH_3)(CH_2CH_2CF_3)\text{—}(CH_2)bNH_2$,
$NH_2(CH_2)a\text{-}(Si(CH_3)_2O)n^1\text{-}(Si(CH_2CH_2CF_3)_2O)n^1\text{-}Si(CH_3)_2\text{—}(CH_2)bNH_2$,
$NH_2(CH_2)a\text{-}(Si(CH_3)_2O)n^1\text{-}(Si(C_3H_6OCOCH=CH_2)(CH_3)O)n^1\text{-}Si(CH_3)_2\text{—}(CH_2)bNH_2$,
$NH_2(CH_2)a\text{-}(Si(CH_3)_2O)n^1\text{-}(Si(C_3H_6OCOCH=CHPh)(CH_3)O)n^1\text{-}Si(CH_3)_2\text{—}(CH_2)bNH_2$,
$NH_2(CH_2)a\text{-}(Si(CH_3)_2O)n^1\text{-}(Si(C_3H_6OCOC_6H_4N_3)(CH_3)O)n^1\text{-}Si(CH_3)_2\text{—}(CH_2)bNH_2$,
$NH_2(CH_2)a\text{-}(Si(CH_3)_2O)n^1\text{-}(Si(C_3H_6SH)(CH_3)O)n^1\text{-}Si(CH_3)_2\text{—}(CH_2)bNH_2$,
$NH_2(CH_2)a\text{-}(Si(CH_3)_2O)n^1\text{-}(Si(Ph)_2O)n^1\text{-}Si(CH_3)_2\text{—}(CH_2)bNH_2$, and
$NH_2(CH_2)a\text{-}(Si(CH_3)_2O)n^1\text{-}(Si(CH_3)(Ph)O)n^1\text{-}Si(CH_3)_2\text{—}(CH_2)bNH_2$.

There is no particular restriction as to the preparation method of the amino compound of the formula (1). For example, there are mentioned: a process in which, with the use of a metal compound such as palladium, rhodium, and ruthenium as a catalyst, a polysiloxane having silyl hydroxyl groups at both ends and a predetermined molecular weight is allowed to react with an unsaturated amine such as 3-amino-1-propene and 4-amino-1-butene; and a process in which such a polysiloxane as was described above is allowed to react with, for example, acrylonitrile in lieu of the unsaturated amine mentioned above to cause catalytic reduction, to introduce, for example, amino propyl groups. Generally, in the production of apolysiloxane, it is also possible to prepare the amino compound of the formula (1) by subjecting a cyclic oligosiloxane to ring-opening polymerization using a disiloxane having an aminoalkyl group as a polymerization terminator.

In the formula (2), $A^1$ represents a divalent organic group having 1 to 20 carbon atoms, such as p-phenylene group, o-phenylene group, m-phenylene group, 4,4'-diphenyl ether group, 4,3'-diphenyl ether group, 4,4'-diphenylene group, 4,3'-diphenylene group, 4,4'-phenylenedimethylene group, 4,4'-thiodiphenylene group, 4,3'-thiodiphenylene group, 4,4'-diphenylthioether group, 4,3'-diphenylthioether group, 4,4'-propylenediphenylene group, 4,3'-propylenediphenylene group, 4,4'-methylenediphenylene group, and 4,3'-methylenediphenylene group. Preferred are p-phenylene group, o-phenylene group, m-phenylene group, 4,4'-diphenyl ether group, 4,3'-diphenyl ether group, 4,4'-diphenylene group, 4,3'-diphenylene group, 4,4'-diphenylthioether group, and 4,3'-diphenylthioether group.

Exemplified as the diamino compound represented by the formula (2) are p-phenylenediamine, o-phenylenediamine, m-phenylenediamine, 4,4'-diaminodiphenylether, 4,3'-diaminodiphenylether, 4,4'-diaminodiphenylene, 4,3'-diaminodiphenylene, 4,4'-diaminodiphenylthioether, 4,3'-diaminodiphenylthioether, 4,4'-diaminodiphenylmethylene, 4,3'-diaminodiphenylmethylene, 4,4'-diaminodiphenylethylene, 4,3'-diaminodiphenylethylene, 4,4'-diaminodiphenylpropylene, and 4,3'-diaminodiphenylpropylene. These can be used either singly or as a mixture.

In the formula (3), B represents a divalent organic group having 1 to 20 carbon atoms, such as p-phenylene group, o-phenylene group, m-phenylene group, 4,4'-diphenylene ether group, 4,3'-diphenylene ether group, 4,4'-diphenylene group, 4,3'-diphenylene group, 4,4'-phenylenedimethylene group, 4,4'-thiodiphenylene group, 4,3'-thiodiphenylene group, 4,4'-propylenediphenylene group, 4,3'-propylenediphenylene group, 4,4'-methylenediphenylene group, and 4,3'-methylenediphenylene group. Preferred as B are p-phenylene group, o-phenylene group, and m-phenylene group, etc.

Examples of the dicarboxylic acid chloride represented by the formula (3) are terephthalic acid chloride, isophthalic acid chloride, phthalic acid chloride, 4,4'-oxybisbenzoic acid chloride, 4,3'-oxybisbenzoic acid chloride, 4,4'-bisbenzoic acid chloride, 4,3'-bisbenzoic acid chloride, 4,4'-thiobisbenzoic acid chloride, 4,3'-thiobisbenzoic acid chloride, 4,4'-methylenebisbenzoic acid chloride, 4,3'-methylenebisbenzoic acid chloride, 4,4'-ethylenebisbenzoic acid chloride, 4,3'-ethylenebisbenzoic acid chloride, 4,4'-propylenebisbenzoic acid chloride, and 4,3'-propylenebisbenzoic acid chloride. These can be used either singly or as a mixture.

The proportions of the amino compound of the formula (1), the diamino compound of the formula (2), and the dicarboxylic acid chloride of the formula (3) to be charged and the reaction conditions are such that the ratio of —$R^1$—$(Si(R^2)(R^3)$—$O)n^1$-$Si(R^2)(R^3)$—$R^1$— to —$A^1$— is within the range of 1:0.01~100, preferably 1:0.1 to 10.

Such reaction conditions are set according to, for example, the processes recited in Japanese Patent Application Laid-Open No. Hei 1-123824, Japanese Patent Application Laid-Open No. Hei 6-313864, and Macromolecules, Vol. 2, p4143 (1989).

For example, it is desired that the molar ratio of the amino compound of the formula (1), the diamino compound of the formula (2), and the dicarboxylic acid chloride of the formula (3) to be charged is suitably selected within the range of 0.001 ~0.090:0.01~0.099:1, preferably 0.01~0.90:0.10~0.99:1.

The polymerization reaction described above can be carried out in a solvent selected from the group consisting of, for instance, DMF, DMAc, tetrahydrofuran (hereinafter, abbreviated as THF) dioxane, acetonitrile, dimethoxyethane, (hereinafter, abbreviated as DME), acetone, methyl ethyl ketone (hereinafter, abbreviated as MEK), diglyme, methyl acetate, ethyl acetate, and mixtures thereof. The use of a mixed solvent is particularly preferred.

They are reacted in accordance with a process in which, after the diamino compound of the formula (2) has been reacted with the dicarboxylic acid chloride of the formula (3), the amino compound of the formula (1) is subjected to reaction, or with a process in which all components are charged to a reactor and reacted at the same time, and either process will do. The chains of segments constituting the resulting copolymer or its molecular weight can be varied by changing the order of charging of these components or timing, slightly varying the ratio, or replacing the solvent with other ones.

With the reactor kept dry by being ventilated with nitrogen gas or air, the reaction(s) may performed at a temperature of from −80° C.~60° C. for 0.1 to 100 hours. The copolymer (A) obtainable through the polymerization described above is a mixture of polymers terminated by an amino group, a carboxyl group, a carboxylic acid, or a carboxylate and having various molecular weight. Usually, the proportion of end groups being amino groups is, relative to all the end groups, preferably about 50%, and usually preferred to exceed 10% but not to exceed 50%. The molecular weight is preferred to fall within the range of from 5,000 to 1,000,000.

The copolymer of the present invention may be produced by allowing the copolymer (A) obtained above to react with an acyl chloride having 2 to 8 carbon atoms, such as acetyl chloride and benzoyl chloride, or by allowing the copolymer (A) to react with a dicarboxylic acid chloride represented by the formula (3) and then with a compound selected from the group consisting of a monovalent hydroxyl group-containing compound having 1 to 8 carbon atoms such as a monohydric alcohol having 1 to 8 carbon atoms, a monovalent amino group-containing compound having 1 to 8 carbon atoms such as a monovalent amine having 1 to 8 carbon atoms, and a mixture thereof. In either case, the resulting copolymers are similarly terminated.

These reactions can be carried out in any of the solvents listed above for use in the polymerization. For example, the amount of the acyl chloride or dicarboxylic acid chloride to be charged is suitably selected according to the proportion of the amino groups remaining at ends of the copolymer (A). For instance, it is preferred that the amount of the acyl chloride or dicarboxylic acid chloride to be charged is 1 to 10 equivalents of amino groups remaining at ends of the copolymer. Each of the reactions may be carried out, for example, at a temperature of −80° C.~60° C. for 1 min.~2 hours. Addition of an alcohol having 1 to 8 carbon atoms following the reaction prevents functional groups from remaining at ends of the copolymer.

The reaction product can be purified by adding an alcohol having 1 to 8 carbon atoms, water, or a mixture thereof to the reaction solution, heating, cooling, and filtering the resulting solution; or by dropping the reaction solution into an alcohol having 1 to 8carbon atoms, water, or a mixture thereof, heating, cooling, and then filtering the resulting mixture; or by repeating either of these procedures.

There is no particular restriction as to the molecular weight of the copolymer obtainable through the process described above, it i s preferably, in terms of the number average molecular weight, about 5,000 to 1,000,000.

The copolymer of the present invention is formed by allowing the copolymer (A) thus obtained to react with the aforementioned acyl chloride and preferably purifying the reaction product, to substitute at least part or all of the amino groups remaining at ends with an acyl cloride residue; or by, after the copolymer (A) obtained has been reacted with the aforementioned dicarboxylic acid chloride, allowing the copolymer (A) to react with a compound selected from the group consisting of a monovalent hydroxyl group-containing compound having 1 to 8 carbon atoms, a monovalent amino group-containing compound having 1 to 8 carbon atoms, and a mixture thereof, to substitute at least part or all of the amino groups remaining at ends. In either case, the resulting copolymers are the same.

The quantity of the amino groups remaining at ends of the copolymer of the present invention can be determined through, for example, the observation of the degree of color change resulting from exposure to high temperature conditions in the presence of oxygen, such as exposure to the air, for a certain period of time. More quantitative ways of measuring may include acid-base titration, the introduction of molecules which, through a quantitative reaction with amino groups, show the absorption of light having a specific wavelength or the emission of fluorescence. Particularly preferred is the following method which is adopted to detect or quantitatively determine amino acid, peptide, or protein, for this method is of high sensitivity and reliability.

Specifically, a fluorescent substance such as fluorescein isothiocyanate (hereinafter, abbreviated as FITC), tetrarhodamine isothiocyanate, fluorescamine, dansyl chloride, and o-phthalic acid chloride is allowed to react with the copolymer of the present invention in a suitable solvent. Thereafter, fluorescent pigments left unreacted are eliminated by washing the reaction solution repetitively. The resulting solution is then dissolved in a suitable solvent and subjected to excitation at a certain wavelength, and the intensity of the fluorescence is measured by a predetermined method. If the concentration is high, the percentage of the residual amino groups may be calculated by measuring the absorption spectrum (intensity) and utilizing the ratio of the absorption spectrum intensity showing the quantity of terminal amino groups remaining in the copolymer before the reaction with the acyl chloride to the absorption spectrum intensity showing the quantity of amino groups remaining in the copolymer of the present invention. In the copolymer of the present invention, it is preferred that the residual amino group quantity figured out from the absorption spectrum intensity ratio is 10% or less. The percentage of residual amino groups per lot can be quantitatively evaluated by observing the degree of color change, that is, by shaping the copolymer thus obtained into a film having a substantially uniform film thickness , exposing the film to a predetermined temperature (e.g., 300° C. or so) for a certain period of time, and quantitatively measuring the shift of the absorption spectrum (the shift of the cut-off wavelength toward longer wavelengths). The behavior under similar thermal stress can also be evaluated by various thermal analysis, or thermomechanical analysis.

Further, the proportion of the residual amino groups relative to all of the end groups of the copolymer of the present invention is measured by, for example, calculating the number of end groups per unit weight using the average molecular weight, and introducing molecules which specifically and quantitatively add to the amino groups, or by carrying out acid-base titration, to quantify the amino groups. In the copolymer of the present invention, the proportion of the residual amino groups relative to all of the end groups is also preferred to be 10% or less, particularly 0 to 5%.

Among copolymers of the present invention obtainable by the above-mentioned production process, preferred is a polydialkylsiloxane/polyamide copolymer having one or more kinds of main chains represented by the formula (4), one end represented by the formula (5) and another end represented by the formula (6) in which the ratio of —$R^1$—$(Si(R^2)(R^3)$—O)$n^1$-Si($R^2$)($R^3$)—$R^1$— as A to a divalent organic group having 1 to 20 carbon atoms as A in the copolymer is within the range of 1:0.01~100 and the proportion of $X^1$ and $X^2$ being hydrogen atoms relative to all of the end groups in the copolymer is 10% or less, preferably 0 to 5%.

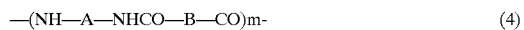

—(NH—A—NHCO—B—CO)m- (4)

—NH—A—NH—$X^2$ (5)

—$X^1$ (6)

In the formulae, $X^1$ and $X^2$ each represents —$COR_4$, —CO—B—$COR^5$ ($R^4$ represents an organic group having 1 to 7 carbon atoms; $R^5$ represents hydroxyl group, —$OR^6$, or —$NHR^6$ ($R^6$ represents an organic group having 1 to 7 carbon atoms); and B represents a divalent organic group having 1 to 20 carbon atoms) or hydrogen atom. A represents —$R^1$—(Si($R^2$)($R^3$)—O)$n^1$-Si($R^2$)($R^3$)—$R^1$—($R^1$ represents a divalent organic group having 1 to 10 carbon atoms; $R^2$ and $R^3$ are the same or different group, each representing an organic group having 1 to 7 carbon atoms; and $n^1$ denotes an integer of 5 to 200) or a divalent organic group having 1 to 20 carbon atoms. B represents a divalent organic group having 1 to 20 carbon atoms. m denotes an integer of 5 to 200.

Even if heat-molded under conditions by which solvent is substantially removed, the above-described copolymer, reduced in the amount of the terminal amino groups, yields a molded article which is substantially uncolored.

Preferred as the main chain represented by the formula (4) are the structures represented by the following formulae and combinations of these structures. In the formulae, Ph represents phenyl group.

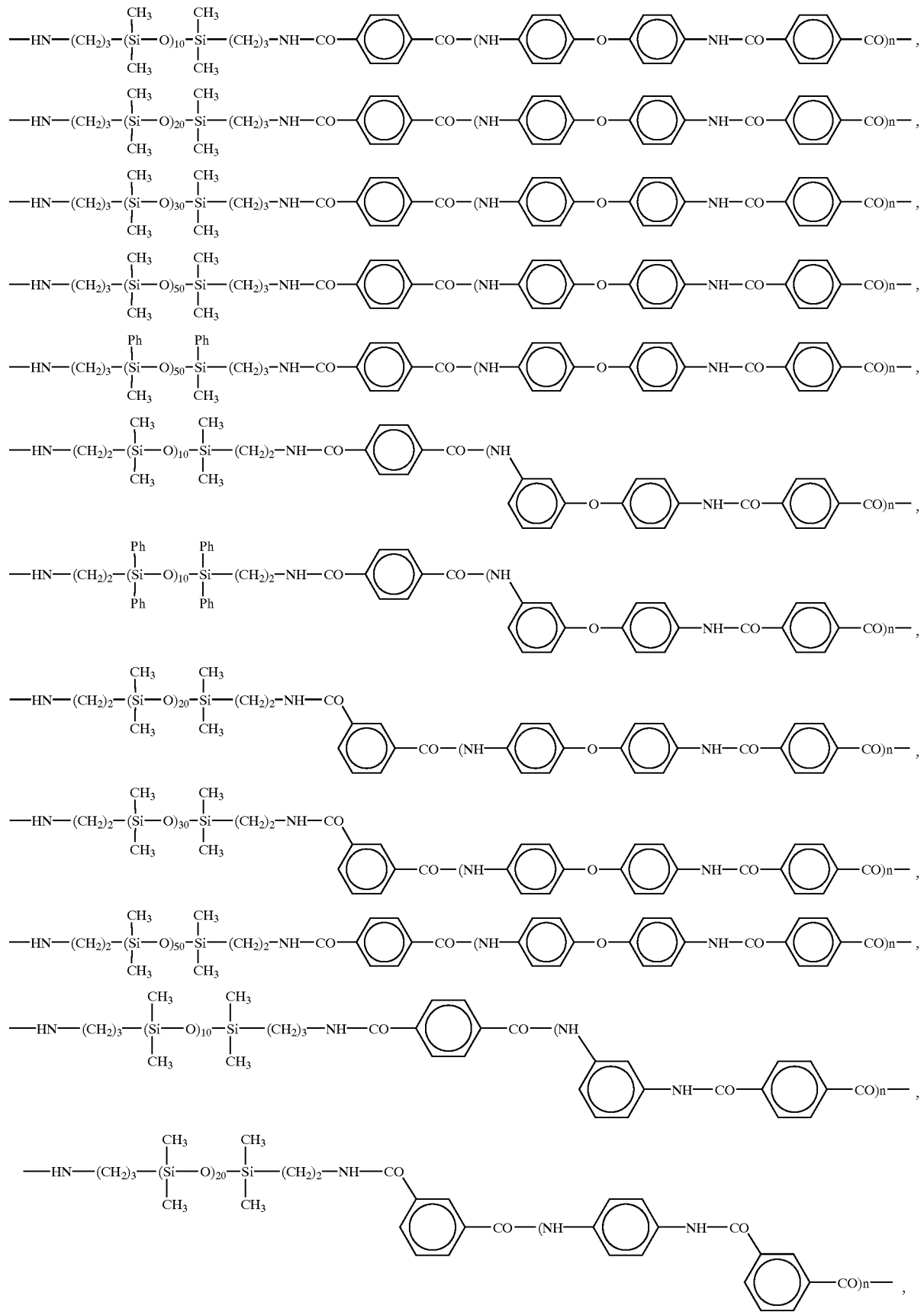

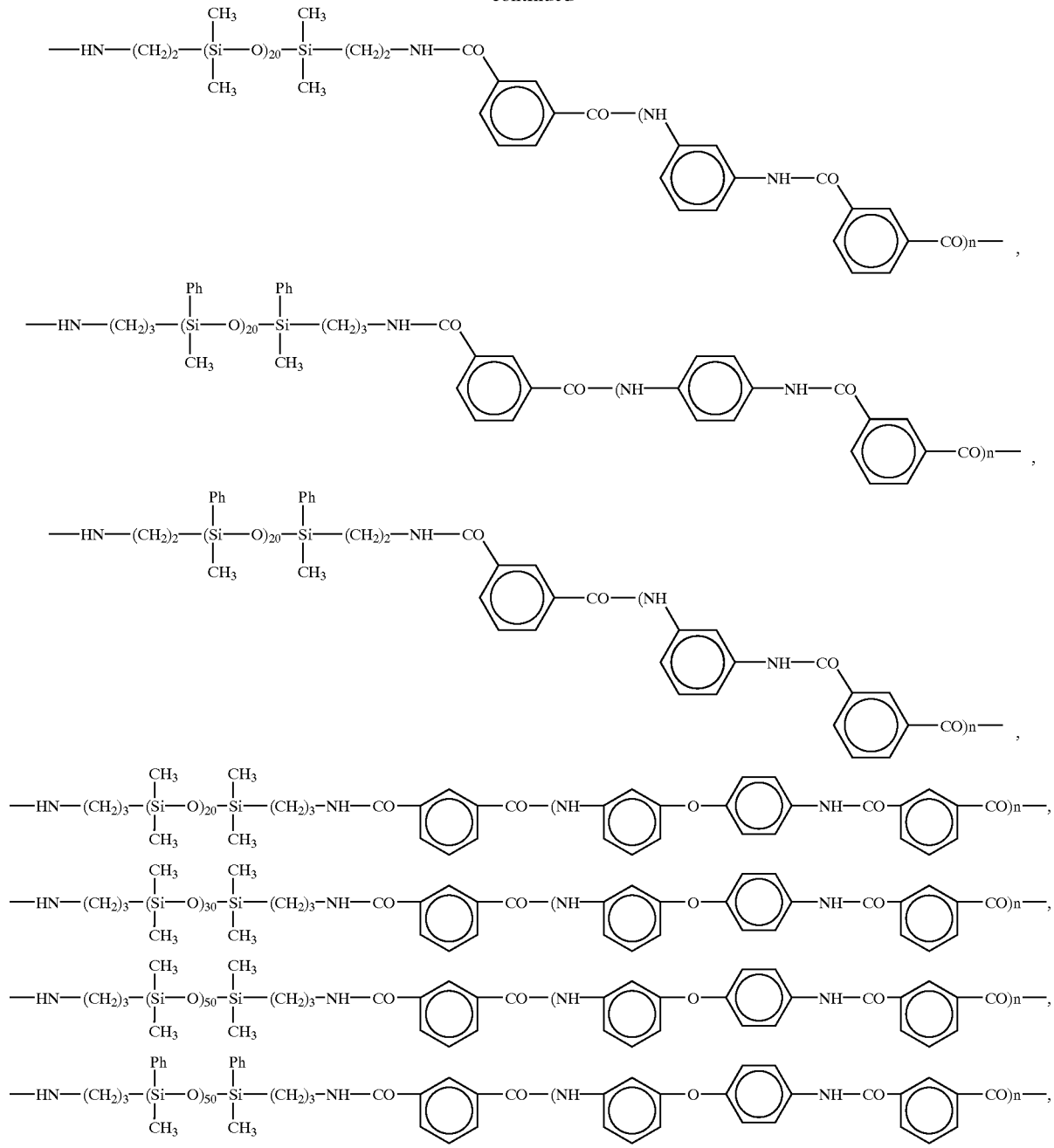

As the end groups represented by $X^1$ and $X^2$ in the formulae (5) and (6), a specific amount or less of hydrogen atoms, and groups represented by the formulae shown below are preferably mentioned:

—COCH$_3$, —COCH$_2$CH$_3$, —CO(CH$_2$)$_2$CH$_3$, —COCH(CH$_3$)$_2$—CO(CH$_2$)CH$_3$, —COCH$_2$CH(CH$_3$)$_2$, —CO(CH$_2$)$_4$CH$_3$, —CO(CH$_2$)$_5$CH$_3$, —CO(CH$_2$)$_6$CH$_3$, —CO(CH$_2$)$_7$CH$_3$, —COCH$_2$CH(C$_2$H$_5$)(CH$_2$)$_3$CH$_3$, —CO(CH$_2$)$_8$CH$_3$, —CO(CH$_2$)$_9$CH$_3$, —CO(CH$_2$)$_{11}$CH$_3$, —CO(CH$_2$)$_{13}$CH$_3$, —CO(CH$_2$)$_{15}$CH$_3$, —CO(CH$_2$)$_{17}$CH$_3$, —CO(CH$_2$)$_{19}$CH$_3$, —CO—B—COOH, —CO—B—COOCH$_3$, —CO—B—COOC$_2$H$_5$, —CO—B—COOC$_3$H$_7$, —CO—B—COOC$_4$H$_9$, —CO—B—COOC$_5$H$_{11}$, —CO—B—COOC$_6$H$_{13}$, —CO—B—COOC$_7$H$_{15}$, —CO—B—CONHC$_2$H$_5$, —CO—B—CONHC$_4$H$_9$, —CO—B—CONHC$_5$H$_{11}$, —CO—B—CONHC$_6$H$_{13}$, and —CO—B—CONHC$_7$H$_{15}$.

In the formulae, B represents -o-C$_6$H$_4$—, -m-C$_6$H$_4$—, -p-C$_6$H$_4$—, -o-C$_6$H$_4$—O-o-C$_6$H$_4$—, -m-C$_6$H$_4$—O-o-C$_6$H$_4$—, -p-C$_6$H$_4$—O-o-C$_6$H$_4$—, -m-C$_6$H$_4$—O-m-C$_6$H$_4$—, -m-C$_6$H$_4$—O-p-C$_6$H$_4$—, -p-C$_6$H$_4$—O-p-C$_6$H$_4$—, -o-C$_6$H$_4$—S-o-C$_6$H$_4$—, -m-C$_6$H$_4$—S-o-C$_6$H$_4$—, -p-C$_6$H$_4$—S-o-C$_6$H$_4$—, -m-C$_6$H$_4$—S-m-C$_6$H$_4$—, -m-C$_6$H$_4$—S-p-C$_6$H$_4$—, -p-C$_6$H$_4$—S-p-C$_6$H$_4$—, -o-C$_6$H$_4$—CH$_2$-o-C$_6$H$_4$—, -m-C$_6$H$_4$—CH$_2$-o-C$_6$H$_4$—, -p-C$_6$H$_4$—CH$_2$-o-C$_6$H$_4$—, -m-C$_6$H$_4$—CH$_2$-m-C$_6$H$_4$—, -m-C$_6$H$_4$—CH$_2$-p-C$_6$H$_4$—, or -p-C$_6$H$_4$—CH$_2$-p-C$_6$H$_4$—.

The copolymer of the present invention is obtained in the form of a mixture being any of a variety of combinations of the main chains and end groups listed above.

The copolymer of the present invention may be dried after its production. For example, the copolymer may be dried, under atmospheric pressure, at a temperature of from room temperature to 150° C., preferably about 70° C. for 1 to 20 hours, preferably 2 to 8 hours, then at a temperature of not higher than 250° C., under reduced pressure by vacuum pumping, for 1 to 7 days. It is also possible to solidify the copolymer of the present invention while molding it in the desired form, for example in a fibrous, hollow-fibrous, or filate form, by wet molding.

The molded article of the present invention is an article obtained by forming a molding material containing at least one of the copolymers of the present invention into a certain shape. In the case of the fabrication of a film article, the solvent-cast method may be employed as the molding method.

The solvent-cast molding may be performed by preparing a solution as the molding material containing 0.5 to 40 wt %, preferably about 10 wt % of the present copolymer in a solvent such as DMAc or DMF, and cast-molding the solution. A cast membrane may be obtained by roughly drying the solution under atmospheric pressure at a temperature from room temperature to 150° C., preferably on a hot plate heated up to about 70° C., for 1 to 20 hours, preferably for 2 to 8 hours, and then at room temperature or a temperature not higher than 250° C., under pressure reduced by vacuum pumping, for 1 to 7 days. The form of the molded articles obtained by the cast method is not limited to a film but may include any of a variety of forms.

In some cases, fabrication of a molded article obtained by this solvent-cast method has the risk of failure in eliminating the solvent contained therein, especially in the case where the solvent to be used is highly polar or has a high boiling point depending on the composition of the copolymer. Therefore, it would be desirable that such article finds its uses other than ophthalmic and medical materials.

The residual solvent in the molded article can be measured by, for example, determining the hydrogen peak due to the solvent by $^1$H-NHR. However, the sensitivity of this method is as low as several percentages, and this method is effective only when the hydrogen peak of the polymer and that of the solvent do not overlap. Other ways of measuring include thermogravimetry (TG) and differential scanning calorimetry (DSC). The former method is such that a change in weight of the solvent contained in the polymer or the polymer itself is measured in the process of elevating the temperature up to the decomposition temperature of the polymer. If the residual solvent contained in the polymer has been evaporated, a change in weight equivalent to the amount of the vaporized solvent may be measured. However, if the decomposition or boiling temperature of the residual solvent is similar to or the same as those of other impurities such as water or the decomposition temperature of the polymer itself, it becomes impossible to recognize a change in weight. On the other hand, the latter method is such that enthalpy changes accompanying the evaporation of the solvent contained in the polymer is measured in the process of elevating the temperature up to the decomposition temperature of the polymer. Basic principle of DSC is similar to TG. In the case of measuring a solvent of high boiling point and high latent heat of evaporation, this method provides measurements with extremely high sensitivity.

Examples of other molding methods include the heat-molding method. This heat-molding method makes it possible to remove most of the solvent inevitably left in the copolymer during the productions or to make the copolymer substantially solvent-free, and therefore is useful particularly for the production of ophthalmic materials such as contact lenses and intraocular lenses and medical materials. In the case of the fabrication of a molded article from a copolymer proposed in the past having a main chain represented by the formula (4) the terminals of which are not treated with an acyl chloride, it was impossible to adopt the heat-molding method. This is because heating causes the degradation or color change of the molded article and this method is unable to make the article substantially solvent-free. In contrast, even if heat-molded, a molding material containing the copolymer of the present invention is inhibited from being colored (decolored) and can yield a molded article which is substantially transparent.

Exemplified as the heat-molding method are hot-press molding, melt-flow molding, and injection molding, and the molding conditions are suitably selected. The shape of the molded article is selected according to the intended use and there is no particular restriction.

The molded article of the present invention may be one that has been crosslinked by energy beam irradiation after the molding. Examples of the energy beam are electron beams, radiation beams, plasma beams, etc. It is also possible to crosslink the molded article by applying an electric field thereto.

It is preferred that the electron beam irradiation is carried out at a dose within the range of from 1 to 1,000 Mrad, particularly from 5 to 100 Mrad. Whether the crosslinking has been effected or not can be confirmed by, after the energy beam irradiation, measuring the softening temperature by thermomechanical analysis (TMA) to check a rise in softening temperature. Moreover, the extent of a rise in softening temperature shows the degree of crosslinking. Whether the crosslinking was effected or not and its degree can also be evaluated by measuring the dynamic viscoelasticity.

The crosslinking makes it possible to further improve the mechanical strength of the molded article without losing the biocompatibility derived from the copolymer of the present invention, and therefore its use in ophthalmic materials and a variety of medical materials is expected.

For imparting hydrophilicity, the surface of the molded article of the present invention, after the molding or electron beam irradiation, may be provided with a membrane containing a copolymer in which the compositional ratio of the hydrophilic monomer unit to the hydrophobic monomer unit is 1:0.01~100, preferably 1:0.1~10. Further, the molded article of the present invention may be an integrally molded one formed by, after the molding or electron beam irradiation, firmly bonding the surface of the molded article with a molded article containing a copolymer in which the compositional ratio of the hydrophilic monomer unit to the hydrophobic monomer unit is 1:0.01~100, preferably 1:0.1~10.

Such hydrophilicity-imparted molded article can be used as a variety of medical materials required to be hydrophilic, particularly as an ophthalmic material such as contact lenses with an improved fit to the eye, intraocular lenses, etc.

Exemplified as the monomer constituting the monomer unit mentioned above are 2-hydroxyethyl acrylate (hereinafter, abbreviated as HEA), 2-hydroxyethyl methacrylate (hereinafter, abbreviated as HEMA), acrylamide (hereinafter, abbreviated as AAm), vinylpyrrolidone (hereinafter, abbreviated as VPD), acrylic acid (hereinafter, abbreviated as AA), and methacrylic acid (hereinafter, abbreviated as MAA). On the other hand, as the hydrophobic monomer constituting the hydrophobic monomer unit, there are mentioned, for example, methyl acrylate (hereinafter, abbreviated as MA), methyl methacrylate (hereinafter, abbreviated as MMA), ethylacrylate (hereinafter, abbreviated as EA), ethyl methacrylate (hereinafter, abbreviated as EMA), propyl acrylate (hereinafter, abbreviated as PA), propyl methacrylate (hereinafter, abbreviated as PMA), butyl acrylate (hereinafter, abbreviated as BA), butyl methacrylate (hereinafter, abbreviated as BMA), lauryl acrylate (hereinafter, abbreviated as LA), lauryl methacrylate (hereinafter, abbreviated as LMA), stearyl acrylate (hereinafter, abbreviated as SA), stearyl methacrylate (hereinafter, abbreviated as SMA), 2-ethylhexyl acrylate (hereinafter, abbreviated as EHA), 2-ethylhexyl methacrylate (hereinafter, abbreviated as EHMA), and styrene (hereinafter, abbreviated as St).

Further, a compound having a side chain represented by the formula (7) is also preferable as the aforementioned monomer.

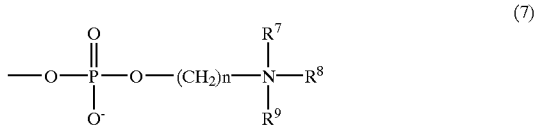

(7)

In the formula, $R^7$, $R^8$, and $R^9$ are the same or different, each representing hydrogen atom or an alkyl group having 1 to 4 carbon atoms. n denotes an integer of 2 to 4.

Preferably employed as a compound having a side chain represented by the formula (7) is 2-(meth)acryloyloxyethyl-2'-trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(vinyloxy)ethyl-2'-(trimethylammonio)ethyl phosphate, 2-(allyloxy)ethyl-2'-(trimethylammonio)ethyl phosphate, 2-(p-vinylbenzyloxy)ethyl-2'-(trimethylammonio)ethyl phosphate, 2-(p-vinylbenzoyloxy)ethyl-2'-(trimethylammonio)ethyl phosphate, 2-(styryloxy)ethyl-2'-(trimethylammonio)ethyl phosphate, 2-(p-vinylbenzyl)ethyl-2'-(trimethylammonio)ethyl phosphate, 2-(vinyloxycarbonyl)ethyl-2'-(trimethylammonio)ethyl phosphate, 2-(allyloxycarbonyl)ethyl-2'-(trimethylammonio)ethyl phosphate, 2-(acryloylamino)ethyl-2'-(trimethylammonio)ethyl phosphate, 2-(vinylcarbonylamino)ethyl-2'-(trimethylammonio)ethyl phosphate, 2-(allyloxycarbonylamino)ethyl-2'-(trimethylammonio)ethyl phosphate, 2-(butenoyloxy)ethyl-2'-(trimethylammonio)ethyl phosphate, 2-(crotonoyloxy)ethyl-2'-(trimethylammonio)ethyl phosphate, ethyl-(2'-trimethylammonioethylphosphorylethyl) fumarate, butyl-(2'-trimethylammonioethylphosphorylethyl) fumarate, or hydroxyethyl-(2'-trimethylammonioethylphosphorylethyl) fumarate. From the viewpoint of, e.g., availability, 2-methacryloyloxyethyl-2'-(triethylammonio)ethyl phosphate (also referred to as 2-methacyloyloxyethylphosphorylcholine) (hereinafter, abbreviated as MPC) is preferably employed.

As the above-mentioned copolymer having a hydrophilic monomer unit andahydrophobic monomer unit, there are mentioned, for example, MPC-MMA copolymer, MPC-EMA copolymer, MPC-PMA copolymer, MPC-BMA copolymer, MPC-LMA copolymer, MPC-SMA copolymer, MPC-EHMA copolymer, MPC-St copolymer, MPC-MA copolymer, MPC-EA copolymer, MPC-PA copolymer, MPC-BA copolymer, MPC-LA copolymer, MPC-SA copolymer, MPC-EHA copolymer, APC-MMA copolymer, APC-BMA copolymer, HEMA-MMA copolymer, AAm-BMA copolymer, AAm-SMA copolymer, VPD-SMA copolymer, VPD-EHMA copolymer, VPD-St copolymer, and HEMA-MA copolymer.

Although there is no particular restriction as to the compositional ratio of the hydrophilic monomer unit to the hydrophobic monomer unit in the above-mentioned copolymer, the ratio of the former to the latter is preferably 1:0.001~100, particularly 1:0.01~10. The molecular weight of such copolymer is usually preferred to fall within the range of, in terms of number average molecular weight, from 1,000~1,000,000.

The above-described hydrophilicity-imparted molded article can be fabricated by, in a single solvent of an alcohol, water, DMAc, DMF, or DMSO, or a mixed solvent thereof, polymerizing the hydrophilic monomer with the hydrophobic monomer in the presence of a suitable radical polymerization initiator such as an azo-type initiator or a peroxide-type initiator to prepare a solution of a copolymer having a hydrophilic monomer unit and a hydrophobic monomer unit, immersing the molded article or the crosslinked molded article after energy beam irradiation in the copolymer solution, and drying the resulting molded article to form a membrane containing the copolymer constituted of the hydrophilic monomer unit and the hydrophobic monomer unit; or by applying the copolymer solution onto the desired surface of the molded article or the crosslinked molded article after energy beam irradiation by coating or spraying, and drying the coat to give a membrane containing the copolymer having a hydrophilic monomer unit and a hydrophobic monomer unit.

Although there is no particular restriction as to the thickness of the membrane comprising the copolymer constituted of a hydrophilic monomer unit and a hydrophobic monomer unit, a thickness of 0.001~100 μm is suitable.

It is also possible to fabricate the hydrophilicity-imparted molded article by molding the copolymer having a hydrophilic monomer unit and a hydrophobic monomer unit in the form of a film, sheet, tube, or filaments, bringing the molded article thus obtained into tight contact with the above-described molded article or the crosslinked molded article after energy beam irradiation, and heat-treating the two articles at a suitable temperature within the range of from room temperature to about 200° C. to bond them together firmly into one piece; or by blending the copolymer of the present invention with the copolymer constituted of a hydrophilic monomer unit and a hydrophobic monomer unit in a conventional manner and then molding the blend into an integrally molded article.

The molded article containing the copolymer comprised of a hydrophilic monomer unit and a hydrophobic monomer unit, and the molded article or the crosslinked molded article after energy beam irradiation can be firmly combined into one piece just by bringing the two components into tight contact.

The surface of the molded article of the present invention may be chemically modified after the molding. Insofar as the surface of the resulting article is chemically modified and provided with substituents whereby a chemical reaction can proceed smoothly, there is no particular restriction as to how the surface is treated.

Exemplified as the way of chemically modifying the surface are chemical treatment with an alkali, an acid, or a chemical modifier; a variety of discharge treatments, such as colona discharge treatment, glow discharge treatment, and low-temperature plasma treatment, in the presence of a gas containing oxygen gas, nitrogen gas, argon gas, tetrafluoro methane gas, etc.; ozone treatment; ionizing active energy ray treatments such as ultraviolet ray or electron beam radiation; and flame treatment.

Moreover, after the above-described chemical modification for providing substituents with which a chemical reaction can proceed smoothly has been effected, the surface of the molded article may be chemically bonded further with a polymer of a monomer composition containing a monomer unit having a group capable of making a covalent bond with the substituents provided on the surface of the molded article.

Examples of a monomer containing a monomer unit having a substituent capable of making a covalent bond for use in the monomer composition are (meth)acrylic acid, aconitic acid, itaconic acid, methaconic acid, citraconic acid, fumaric acid, maleic acid, methaconic acid, vinylsulfonic acid, acrylamide-2-methylpropane sulfonate, vinylsulfonic acid, and a variety of their metal salts, 2-hydroxyethyl (meth)acrylate, monoglycerol methacrylate, N-(tris (hydroxymethyl)methyl)acrylamide, maleic anhydride, glycidl (meth)acrylate, allylamine, aminoethyl (meth)acrylate, and glycidyl methacrylate.

In the monomer composition, examples of preferred monomers that are further copolymerizable may include hydrophilic macromonomers such as N,N-dimethylaminopropyl (meth)acrylamide, N,N-dimethylaminoethyl (meth)acrylamide, N,N-dimethylaminoethyl (meth)acrylate, their quarternary salts, 2-vinylpyridine, 3-vinylpyridine, 4-vinylpyridine, 2-vinylimidazole, N-methyl-2-vinylimidazole, N-vinylimidazole, (meth)acrylamide, N-methyl (meth) acrylamide, N,N-dimethyl (meth)acrylamide, N-ethyl (meth)acrylamide, N-isopropl (meth)acrylamide, N-t-butyl (meth)acrylamide, vinyl methyl ether, polyethylene glycol (meth)acrylate, N-vinylpyrrolidone, N-(meth) acryloylpyrrolidone, acryloylmorpholine, maleic imide, and vinyl acetate; styrenic monomers such as styrene, methylstyrene, chloromethylstyrene, and aminostyrene; monoalkyl (meth)acrylates such as methyl (meth)acrylate, ethyl (meth)acrylate, butyl (meth)acrylate, dodecyl (meth) acrylate, cetyl (meth)acrylate, stearyl (meth)acrylate, cyclohexyl (meth)acrylate, and 2-ethylhexyl (meth)acrylate; reactive functional group-containing (meth)acrylates such as glycidyl (meth)acrylate, and (meth) acryloyloxyethyltrimethoxysilane; urethane-modified (meth)acrylates such as 2-(meth) acryloyloxyethylbutylurethane, 2-(meth) acryloyloxyethylbenzylurethane, and 2-(meth) acryloyloxyethylphenylurethane; ethyl vinyl ether, butyl vinyl ether, vinyl acetate, vinyl chloride, vinylidene chloride, ethylene, propylene, isobutylene, diethyl fumarate, diethyl maleate, acrylonitrile,vinylbenzylamine, various hydrophobic macromonomers, and compounds having a side chain represented by the formula (7).

Examples of the compounds having a side chain represented by the formula (7) are MPC, 3-(meth) acryloyloxypropyl-2'-(trimethylammonio)ethyl phosphate, 4-(meth) acryloyloxybutyl-2'-(trimethylammonio) ethyl phosphate, 5-(meth)acryloyloxypentyl-2'-(trimethylammonio)ethyl phosphate, 6-(meth) acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth) acryloyloxyethyl-2'-(tributylammonio)ethyl phosphate, 2-(meth)aryloyloxypropyl-2'-(trimethylammonio)ethyl phosphate, 2-(meth)acryloyloxybutyl-2'-(trimethylammonio)ethyl phosphate, 2-(meth) acryloyloxypentyl-2'-(trimethylammonio)ethyl phosphate, 2-(meth)acryloyloxyhexyl-2'-(trimethylammonio)ethyl phosphate, 2-(vinyloxy)ethyl-2'-(trimethylammnoio)ethyl phosphate, 2-(allyloxy)ethyl-2'-(trimethylammonio)ethyl phosphate, 2-(p-vinylbenzyloxy)ethyl-2'-(trimethylammonio)ethyl phosphate, 2-(p-vinylbenzoyloxy) ethyl-2'-(trimethylammonio)ethyl phosphate, 2-(styryloxy) ethyl-2'-(trimethylammonio)ethyl phosphate, 2-(p-vinylbenzyl)ethyl-2'-(trimethylammonio)ethyl phosphate, 2-(vinyloxycarbonyl)ethyl-2'-(trimethylammonio)ethyl phosphate, 2-(allyloxycarbonyl)ethyl-2'-(trimethylammonio)ethyl phosphate, 2-(acryloylamino) ethyl-2'-(trimethylammonio)ethyl phosphate, 2-(vinylcarbonylamino)ethyl-2'-(trimethylammonio)ethyl phosphate, 2-(allyloxycarbonylamino)ethyl-2'-(trimethylammonio)ethyl phosphate, 2-(butenoyloxy)ethyl-2'-(trimethylammonio)ethyl phosphate, 2-(crotonoyloxy) ethyl-2'-(trimethylammonio)ethyl phosphate, ethyl-(2'-trimethylammonioethylphosphorylethyl) fumarate, butyl-(2'-trimethylammonioethylphosphorylethyl) fumarate, and hydroxyethyl-(2'-trimethylammonioethylphosphorylethyl) fumarate.

Further, as a polymer obtainable by copolymerizing the monomer position mentioned above, a polymer having both a side chain represented by the formula (7) and amino group is preferred.

Although there is no particular restriction as to the content of the monomer containing a monomer unit having a substituent capable of making a covalent bond, it is preferred to be, per 100 parts by weight of all the monomer components in the monomer composition, 0.001 to 50 parts by weight, particularly 0.1 to 10 parts by weight.

The polymer obtained by polymerizing the above-mentioned monomer composition may be formed according to a publicly known solution polymerization method, emulsion polymerization method, or suspension polymerization method. In any case, the polymer can be obtained by the radical polymerization under the conditions of a polymerization temperature of 0~100° C. and a polymerization time of 10 minutes 48 hours, in a polymerization system optionally gas-exchanged with such an inert gas as nitrogen, carbon dioxide, and helium or put in an atmosphere of such inert gas.

Exemplified as a polymerization initiator to be used in the radical polymerization are 2,2'-(2-amidinopropane) dihydrochloride, 4,4'-azobis(4-cyanovaleric acid), 2,2'-azobis(2-(5-methyl-2-imidazolin-2-yl)propane) dihydrochloride, 2,2'-azobis(2-(2-imidazolin-2-yl)propane) dihydrochloride, 2,2'-azobisisobutylamide dihydrate, ammonium persulfate, potassium persulfate, benzoyl peroxide, diisopropylperoxydicarbonate, t-butylperoxy-2-ethylhexanoate, t-butylperoxypivalate, t-butylperoxydiisobutylate, lauroyl peroxide, azobisisobutylonitrile (hereinafter, abbreviated as AIBN), 2,2'-azobis(2,4-dimethylvaleronitrile), and t-butylperoxyneodecanoate (e.g., trade name "PERBUTYL ND" manufactured by NOF Corporation) (hereinafter, abbreviated as P-ND), and these can be used either singly or as a mixture. As the radical polymerization initiator, a variety of redox-type accelerators may also be employed.

The radical polymerization initiator may be used in an amount of 0.01 to 5.0%, by weight relative to the sum of the initiator and the monomer component(s).

The polymer can be purified by a publicly known reprecipitation method, dialysis method, or ultrafiltration method.

It is preferred that the polymer thus obtained has a weight average molecular weight of 1,000~5,000,000, particularly 10,000~500,000.

It is possible to allow the polymer to react with the aforementioned molded article, depending on the species of the substituent introduced into the polymer and capable of making a chemical bond, and on the species of the substituent introduced onto the surface of the molded article due to which a chemical reaction smoothly proceeds.

For example, in the case where the polymer is one that has an amino group and carboxyl groups have been introduced onto the surface of the molded article, with the aid of a variety of condensation agents such as dicylohexylcarbodiimide, or a water-soluble carbodiimide, these substituents may be amide-bonded each other. In the case where the polymer is one that has an epoxy group and amino groups have been introduced onto the surface of the molded article, chemical bonds therebetween may be formed by heating.

The ophthalmic material of the present invention is a material for use in contact lenses, intraocular lenses, etc., which is one or more of the molded articles having been processed in any desired shape. With the material that has been processed in the desired shape, contact lenses or intraocular lenses may be produced in accordance with a publicly known process. Moreover, the ophthalmic material such as contact lenses and intraocular lenses thus obtained may be subjected to a variety of publicly known treatments such as surface treatment.

The medical material of the present invention is a material obtained by processing at least one of the various molded articles described above in the desired form so as to be available for use in, e.g., artificial heart valves, artificial hearts, lead wires for heart pacemakers, and antithrombotic materials of varied forms. Any of publicly known processing techniques can be employed.

In the various molded articles of the present invention described above, the proportions of the silicone segment and the aramid segment are controllable arbitrarily. Therefore, the degree of flexibility in adjusting mechanical strength and other physical properties to the required levels is high. Further, the molded articles of the present invention are heat-moldable and heat-fusible. They are thus suitable for manufacturing a one-piece product such as an intraocular lens that is required to have different properties from part to part. That is, elements having best composition for each part may readily be assembled and shaped by thermal processing.

For example, the center part of the optical member of the intraocular lens may be made of a resin having high content of a silicone segment having aromatic groups such as a phenyl group, for giving high refractive index and softness. The peripheral part of the optical member may be made of a resin having high content Of a silicone segment having a lower alkyl group such as dimethylsiloxane for the purpose of imparting softness even at the low refractive index. Since its fixation members are required to have high strength, they may be made of a resin having high content of the amide segment. The desired intraocular lens may be obtained by combining these components into one piece. Further, fusion molding with other base materials may readily be performed.

The cosmetic composition of the present invention contains the copolymer of the present invention, any of the various molded articles thereof, or a mixture of these. Mentioned as examples of cosmetics are ultraviolet ray blocking agents, cosmetics for skin, lipsticks, nail lacquers, mascara, shampoo, hair styling lotions, and hair lacquers.

Incorporation of the cosmetic composition of the present invention into cosmetics imparts not only excellent water resistance, oil resistance, durability, and ultraviolet ray blocking properties but also the capability of keeping the style of for example hair thereto. In the cosmetic composition, the proportion of the copolymer of the present invention and/or any of the various molded articles of the present invention may be suitably selected according to the kind of the cosmetic product to be produced or its purpose. Usually, the desired effect may be obtained by incorporating the copolymer of the present invention and/or any of the various molded articles of the present invention in such an amount as to account for 0.05 to 50% by weight of the total amount of the resulting cosmetic product.

To the cosmetic composition of the present invention may be added various drugs and medicines or quasi-drugs which are normally incorporated into cosmetics, such as oils and fats, essential oils, galenicals, organic acids, inorganic salts, inorganic acids, esters, alcohols, amino acids, enzymes, animal and vegetable extracts, surfactants, antioxidants, sterilizers, ultraviolet ray blocking agents, pigments, and flavors, in suitable amounts provided that the desired effect of the copolymer of the present invention is not adversely affected.

The electronic material of the present invention contains the copolymer of the present invention, any of the various molded articles of the present invention, or a mixture thereof. Thus, the material suitably has excellent fatigue resistance, wear resistance, creep characteristics, heat resistance, water resistance, dimensional stability, vibration absorbing properties, self-extinguishability (flame retardancy), etc.

In the electronic material of the present invention, the proportion of the copolymer of the present invention and/or any of the various molded articles of the present invention is suitably selected depending on the kind of electronic material. Moreover, besides the copolymer of the present invention and others, to the electronic material maybe added other components and a variety of additives depending on the type of the electronic material. It is also possible to modify the characteristics of the surface to a large extent by, for example, subjecting the surface to hydrophilization treatment using, e.g., the above-described hydrophilic-hydrophobic copolymer or the like.

Since the present copolymer has a dialkylsiloxane unit and an amide unit and part or all of the amino groups remaining at ends have been treated, the copolymer is excellent in biocompatibility and mechanical strength, and the molded article thereof is excellent also in heat resistance and available for use in a wide range of medical materials, ophthalmic materials, cosmetic materials, electronic materials, etc.

Since the various molded articles of the present invention are substantially made of the copolymer of the present invention, they are excellent in biocompatibility, mechanical strength, and heat resistance, and substantially free from solvent inevitably comes into the production system. Accordingly, the molded articles of the present invention are useful for fibers, powders, sheets, laminated sheets, tubes, artificial heart valves for medical use, artificial hearts, lead wires for heart pacemakers, contact lenses, intraocular lenses, etc.

Further, since the cosmetic composition of the present invention shows not only excellent water resistance, oil resistance, durability, and ultraviolet ray blocking properties when applied onto to the skin, but also the capability of keeping the shape of hair, it is available for use in various cosmetic products such as ultraviolet ray blocking agents, cosmetics for skin, lipsticks, nail enamels, mascara, shampoo, hair styling lotions, and hair lacquers.

Furthermore, in the field of, e.g., electronics and optelectronics, the electronic material of the present invention is useful as an electricity insulating material or varnish having both heat resistance and flexibility, a motor, an infilling resin of a transformer, a cable covering, an optical fiber (core/clad layer) material, an alignment film for liquid crystal devices, a spacer for liquid crystal devices, a sealing agent for liquid crystal devices, an optical connector, a conductive elastic connector, an optical louver, a binder resin for electrophotographic printer-use (color) toner, a toner for (color)copying machines/a raw material of a transfer (heat roll) drum, a multilayer circuit board, or a material for transistor protecting layers.

The copolymer and various molded articles of the present invention can be utilized for other general applications, such as adhesives/pressure sensitive adhesives (solvent-free type, room temperature-curing type), paints, coating agents, solid fuel binders, water resistant/chemical resistant covering films (cold application type), sealing agents for construction/engineering, automobile windshield adhesion sealing agents, materials for footwear (soles, heels), floor materials, industrial elastic materials (car bodies, bumpers for cars, belts, hoses, rubber vibration isolators, packing), elastic fiber raw materials for tires, synthetic leather, leather impregnants, a variety of foam materials, reactive modifiers (reactive softeners, plasticizers, crosslinking auxiliaries, grafting agents) for rubber or plastics, soil stabilizing and improving agents, fiber treatment agents, rubber asphalt, gas turbine parts, and coating agents for engine parts.

EXAMPLES

Hereinafter, the present invention will be described in further detail referring to examples, test examples, and comparative examples, but the present invention is not limited thereto.

Each measurement in examples was carried out under the conditions as specified below.

<Measurement of Molecular Weight>

The molecular weight was determined by GPC. The conditions for GPC are as specified below.

GPC system: SC-8020, SD-8013, CCPE-II, AS-8010, CO-8010, and PS-8010 manufactured by Tosoh Corporation.

Column: Mixed-B x 2 manufactured by Polymer Laboratories

RI detector: L-3300RI manufactured by Hitachi Ltd.

Column oven temperature: 60° C.

Eluent: DMAc/MEK=3/10 (volume)+10 mM LiCl

Standard sample: converted using a calibration curve of standard polystyrene

<$^1$H-NMR Measurement>

NMR system: JEOL JNM-EX 270 FT-NMR

Solvent: DMF-$d_6$:$CCl_4$=3:7 (volume ratio)

Base peak: peak due to >Si($CH_3$)$_2$ was set at 0.0749 ppm

<Measurement of Refractive Index>

Measured by an Abbe's refractometer (manufactured by Atago Co., Ltd., 2T-Model).

Comparative Example 1

1.00 g (0.005 mol) of 3,4'-diaminodiphenyl ether (hereinafter, abbreviated as 3,4'-DAPE), 4.2 g (0.0025 mol) of bis(aminopropyl)polydimethylsiloxane (hereinafter, abbreviated as PDMS-d$NH_2$) (number average molecular weight: 1680), 1.52 g (0.015 mol) of triethylamine, 1.52 g (0.0075 mol) of isophthalic chloride (hereinafter, abbreviated as IPC), and 50 ml of a mixed solvent (DMAc:THF=1:1) were mixed together. Then, the mixture was allowed to undergo reactions at 0° C., stirred for 20 minutes, and reacted for another 70 minutes at room temperature. The reaction solution thus obtained was poured into 100 ml of methanol to isolate a polymer.

After having been dissolved in a DMAc solvent, the polymer obtained was filtered with a 0.5 μm membrane filter and subjected to reprecipitation purification in methanol twice to give 5.81 g (yield: 94.1%) of a purified polymer. The purified polymer was dried under reduced pressure, to obtain a polydimethylsiloxane/polyamide copolymer. Having a siloxane component content of about 70% by weight, the polymer thus obtained will be hereinafter abbreviated as PN-17-70. The molecular weight and the refractive index of PN-17-70 were determined by GPC. The results are shown in Table 1.

Example 1

1.00 g (0.005 mol) of 3,4'-DAPE, 4.2 g (0.0025 mol) of PDMS-d$NH_2$ (number average molecular weight: 1680), 1.52 g (0.015 mol) of triethylamine, 1.52 g (0.0075 mol) of IPC, and 50 ml of a mixed solvent (DMAc:THF=1:1) were mixed together. Then, the mixture was allowed to undergo reactions at 0° C., stirred for 20 minutes, and reacted for another 70 minutes at room temperature. Thereafter, to the resulting solution was added a mixed solution of 0.059 g (0.00075 mol) of acetyl chloride and 1 ml of the mixed solvent dropwise, and the mixture was stirred for 30 minutes. At 0° C., to the mixture were added 0.076 g (0.00075 mol) of triethylamine and 1 ml of the mixed solvent, and the resulting mixture was stirred for 30 minutes. The reaction solution thus obtained was poured into 100 ml of methanol to isolate a polymer.

After having been dissolved in a DMAc solvent, the polymer obtained was filtered with a 0.5 μm membrane filter and subjected to reprecipitation purification from methanol twice to give 5.81 g (yield: 86.5%) of a purified polymer. The purified polymer was then dried under reduced pressure, to give a polydimethylsiloxane/polyamide copolymer. Having a siloxane component content of about 70% by weight, the polymer thus obtained will be hereinafter abbreviated as P-17-70. The molecular weight as determined by GPC and its refractive index measured are shown in Table 1.

The results of $^1$H-NMR were 0.0749 ppm (s, >Si($CH_3$)$_2$), 0.6 ppm (t, >Si—$CH_2$CCN<), 1.6 ppm (m, >Si—$CCH_2$CN<), 3.3 ppm (m, >Si—$CCCH_2$N<), 6.6–8.7 ppm (m, Ph), 8.3, 10.3 ppm (s, —NHCO—), and 2.74, 2.91, 7.91 (DMF-$d_6$), indicating that the main chain of the polymer obtained was a mixture having the following structure. $n^1$ is 20.2 on average.

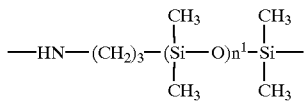 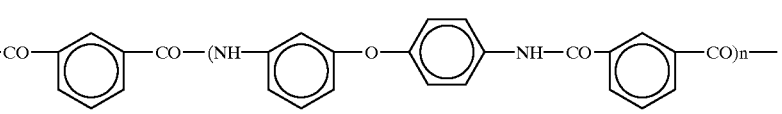

Thereafter, the quantity of the amino groups remaining at ends of P-17-70 obtained was determined in the following manner (FITC method).

Each of 1 g of the polymer P-17-70 and 1 g of the polymer PN-17-70 synthesized in Comparative Example 1 were separately dissolved in 10 g of DMAc, and 0.01 g of FITC (fluorescein isothiocyanate) was added to each mixture and dissolved completely. Then, each mixture was stirred at room temperature for 30 minutes and poured into 100 ml of methanol to reprecipitate the resulting polymer, and unreacted FITC was removed therefrom by washing. After having been dissolved in 10 g of DMAc, each polymer was reprecipitated in 100 ml of methanol and washed again. With the absorbance of the washing liquid kept measured, the reprecipitation and washing were repeated until the absorbance at 490 nm became equivalent to that of the solvent itself. P-17-70 and PN-17-70 were reprecipitated and washed for 16 times and 20 times, respectively. At this point, each polymer was dried in a vacuum oven at 120° C. for 24 hours. After drying, 0.1 wt % DMAc solutions were prepared and the absorbance of each solution at 490 nm was measured. The amount of the amino groups remaining in P-17-70 was determined utilizing the values obtained above in accordance with the following formula. (absorbance of P-17-70)/(absorbance of PN-17-70)=0.02/0.87=0.023

Therefore, the percentage of the residual amino groups left unreacted in P-17-70 was 2.3% of that of the polymer prepared in Comparative Example 1, indicating that the proportion of $X^1$ and $X^2$ in the formulae (5) and (6) being hydrogen atoms was 10% or less relative to all of the end groups of the copolymer obtained.

Examples 2 to 4

A polydimethylsiloxane/polyamide copolymer was synthesized in the same manner as in Example 1 with the exception that the blending ratio of 3,4'-DAPE, PDMS-dNH$_2$, and IPC were changed as shown in Table 1. The yield, molecular weight, and the refractive index were measured in the same manner as in Example 1. The results are shown in Table 1. Based on the proportion of the siloxane component in each copolymer obtained, the copolymer of Example 2, the copolymer of Example 3, and the copolymer of Example 4 will be hereinafter abbreviated as P-17-20, P-17-50, and P-17-80, respectively.

Example 5

6.01 g (0.03 mol) of 3,4'-DAPE, 40.5 g (0.045 mol) of PDMS-dNH$_2$ (number average molecular weight: 900), 15.2 g (0.15 mol) of triethylamine, 15.2 g (0.075 mol) of IPC, and 250 ml of a mixed solvent (DMAc:THF=1:1) were mixed together. Then, the mixture was allowed to undergo reactions at 0° C., stirred for 30 minutes, and reacted at room temperature for another 60 minutes. To the resulting solution was added a mixed solution of 0.59 g (0.0075 mol) of acetyl chloride and 10 ml of the mixed solvent mentioned above dropwise, and the mixture was stirred for 5 minutes. At 0° C., to the mixture were added 0.76 g (0.0075 mol) of triethylamine and 10 ml of the mixed solvent, and the mixture was stirred for 30 minutes. The reaction solution thus obtained was poured into 100 ml of methanol to isolate a polymer.

After having been dissolved in a DMAc solvent, the polymer was filtered with a 0.5 μm membrane filter and subjected to reprecipitation purification from methanol twice to give 52.7 g (yield: 85.3%) of a purified polymer. The purified polymer was dried under reduced pressure, to give a polydimethylsiloxane/polyamide copolymer. Having a siloxane component content of about 70% by weight, the polymer thus obtained will be hereinafter abbreviated as P-9-70. The molecular weight measured by GPC and the refractive index of P-9-70 were determined. The results are shown in Table 1.

Example 6

11.13 g (0.055 mol) of 3,4'-DAPE, 60.0 g (0.02 mol) of PDMS-dNH$_2$ (number average molecular weight: 3,000), 15.2 g (0.15 mol) of triethylamine, 15.2 g (0.075 mol) of IPC, and 250 ml of a mixed solvent (DMAc:THF=1:1) were mixed together. Then, the mixture was allowed to undergo reactions at 0° C., stirred for 30 minutes, and reacted at room temperature for another 60 minutes. To the resulting solution was added a mixed solution of 0.59 g (0.0075 mol) of acetyl chloride and 10 ml of the mixed solvent mentioned above dropwise, and the mixture was stirred for 5 minutes. At 0° C., to the mixture were added 0.76 g (0.0075 mol) of triethylamine and 10 ml of the mixed solvent, and the mixture was stirred for 30 minutes. The reaction solution thus obtained was poured into 100 ml of methanol to isolate a polymer.

After having been dissolved in a DMAC solvent, the polymer was filtered with a 0.5 μm membrane filter and subjected to reprecipitation purification from methanol twice to give 75.5 g (yield: 93.5%) of a purified polymer. The purified polymer was dried under reduced pressure, to give a polydimethylsiloxane/polyamide copolymer. Having a siloxane component content of about 70% by weight, the polymer thus obtained will be hereinafter abbreviated as P-30-70. The molecular weight measured by GPC and the refractive index of P-30-70 were determined. The results are shown in Table 1.

Example 7

Except that 5.0 g (0.0025 mol) of bis(aminopropyl) methylphenylpolysiloxane (phenyl group content: 5.2 mol %, molecular weight: 2,000) (hereinafter, abbreviated as MPhPS-dNH$_2$) was employed in place of PDMS-dNH$_2$, polymerization, post-treatment, and measurements were carried out in the same manner as in Example 1. The polymer obtained will be hereinafter abbreviated as P-P-20-70. The results of analysis are shown in Table 1.

Test Example 1

According to JIS K 7210 (ASTM D 1238), the melt flow rate (M.F.R.) of the copolymer synthesized in Example 1 was measured. The result is shown in Table 1.

Figure 3:
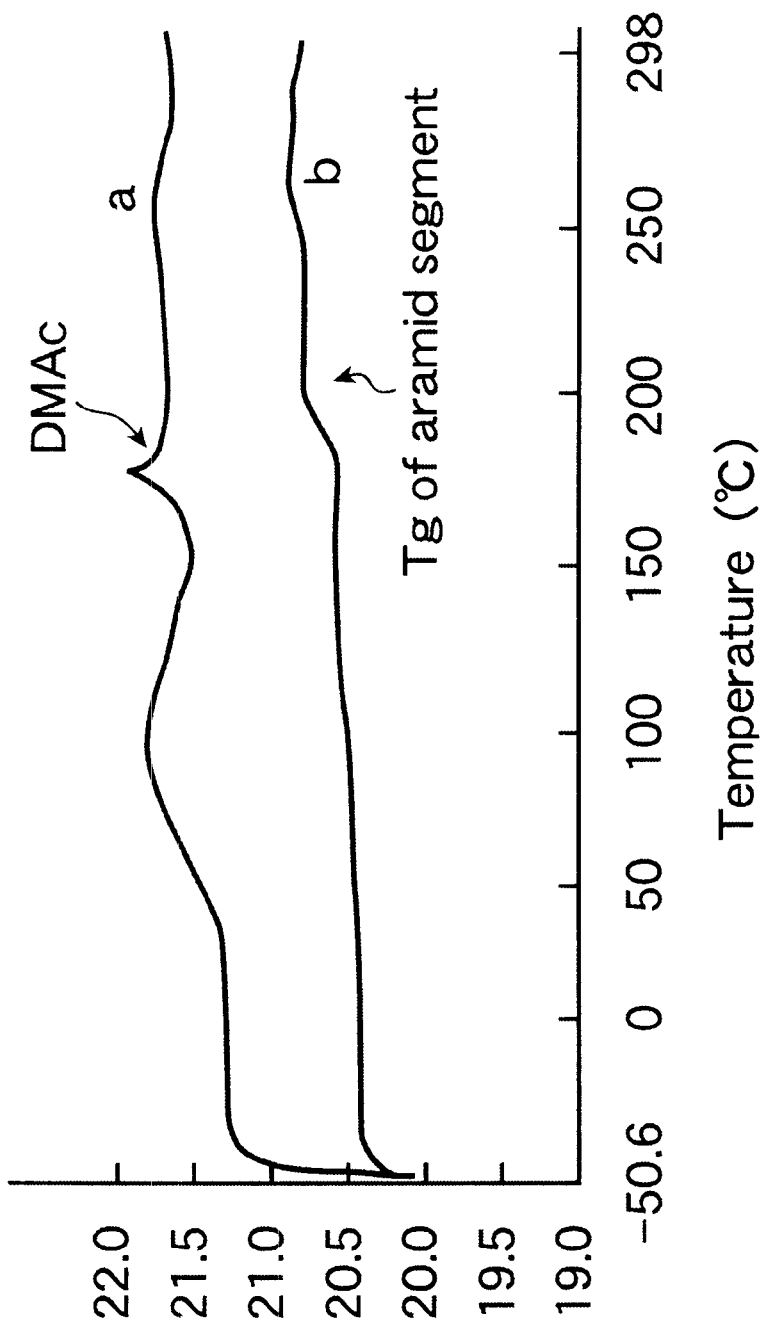
FIG. 3 is a graph showing the results of analysis by a differential scanning calorimeter made on the p-17-20 cast membrane in Example 8 and the p-17-70 film in Example 9.

According to JIS K 7199 (ASTM D 3875), the flowability (viscosity) of each of the copolymers synthesized in Examples 1 to 7 and Comparative Example 1 was measured using a capillary rheometer. Each copolymer was molded into rods having a diameter of 1 mm at 220° C. (orifice diameter: 1 mm), for flowability measurement. As a result, an extremely large decrease in strength was observed only for PN-17-70 synthesized in Comparative Example 1. In addition, only PN-17-70 turned light brown and its surface was found to be sticky like a silicone oil, revealing that decomposition of PN-17-70 in which the terminal amino groups have not been treated is greatly accelerated when exposed to high temperatures, particularly together with application of mechanical stress.

example, the result of measurement by a differential scanning calorimeter made on the cast membrane of P-17-70 is shown in FIG. 3 as a.

Example 9

Each of the polydimethylsiloxane/polyamide copolymers synthesized in Examples 1 to 4 was pressed under atmospheric pressure by a hot presser heated up to 150 to 250° C. (manufactured by Toyo Seiki Seisaku-sho, Ltd., Mini testpress-10) to fabricate a film having the desired thickness.

The films obtained above were subjected to thermogravimetry using a thermogravimeter (manufactured by

TABLE 1

| | | Example 1 | Example 2 | Example 3 | Example 4 | Example 5 | Example 6 | Example 7 | Comp. Ex. 1 |
|---|---|---|---|---|---|---|---|---|---|
| Starting | 3,4'-DAPE | 1.00 | 14.0 | 12.0 | 5.00 | 6.01 | 11.13 | 1.00 | 1.00 |
| material | PDMS-dNH$_2$ | 4.20 | 8.43 | 25.2 | 84.1 | 40.5 | 60.0 | 5.00 | 4.20 |
| | IPC | 1.52 | 15.2 | 15.2 | 15.2 | 15.2 | 15.2 | 1.52 | 1.52 |
| Abbreviation of copolymer | | P-17-70 | P-17-20 | P-17-50 | P-17-80 | P-9-70 | P-30-70 | P-P-20-70 | PN-17-20 |
| Yield (g) | | 5.81 | 31.8 | 45.3 | 93.3 | 52.7 | 75.5 | 6.10 | 5.81 |
| Yield (%) | | 86.5 | 98.8 | 96.3 | 94.5 | 85.3 | 93.5 | 81.1 | 94.1 |
| Mw | | 87000 | 149000 | 79000 | 110000 | 39000 | 141000 | 81000 | 87000 |
| Mw/Mn | | 2.08 | 1.92 | 2.55 | 2.52 | 1.82 | 3.99 | 1.95 | 2.08 |
| M.f.R | | 7.4 | — | — | — | — | — | — | — |
| Refractive index $n_\alpha^{20}$ | | 1.49 | 1.60 | 1.54 | 1.46 | 1.49 | 1.47 | 1.58 | 1.49 |

PDMS-dNH$_2$ Number Average Molecular Weight: 900 (Example 5), 3000 (Example 6), 1680 (Examples 1 to 4), 2000 (Example 7); In Example 7, replaced with MPhPS-dNH$_2$ Example 8

Each of the polydimethylsiloxane/polyamide copolymers synthesized in Examples 1 to 4 was dissolved in DMAc to prepare a 10 wt % solution. After having been filtered with a 0.5 μm membrane filter, each solution was spread on a petri dish made of fluororesin (diameter: 10 cm) and heated on a hot plate for 6 hours to form a cast membrane (thickness: about 100 μm).

Figure 2:
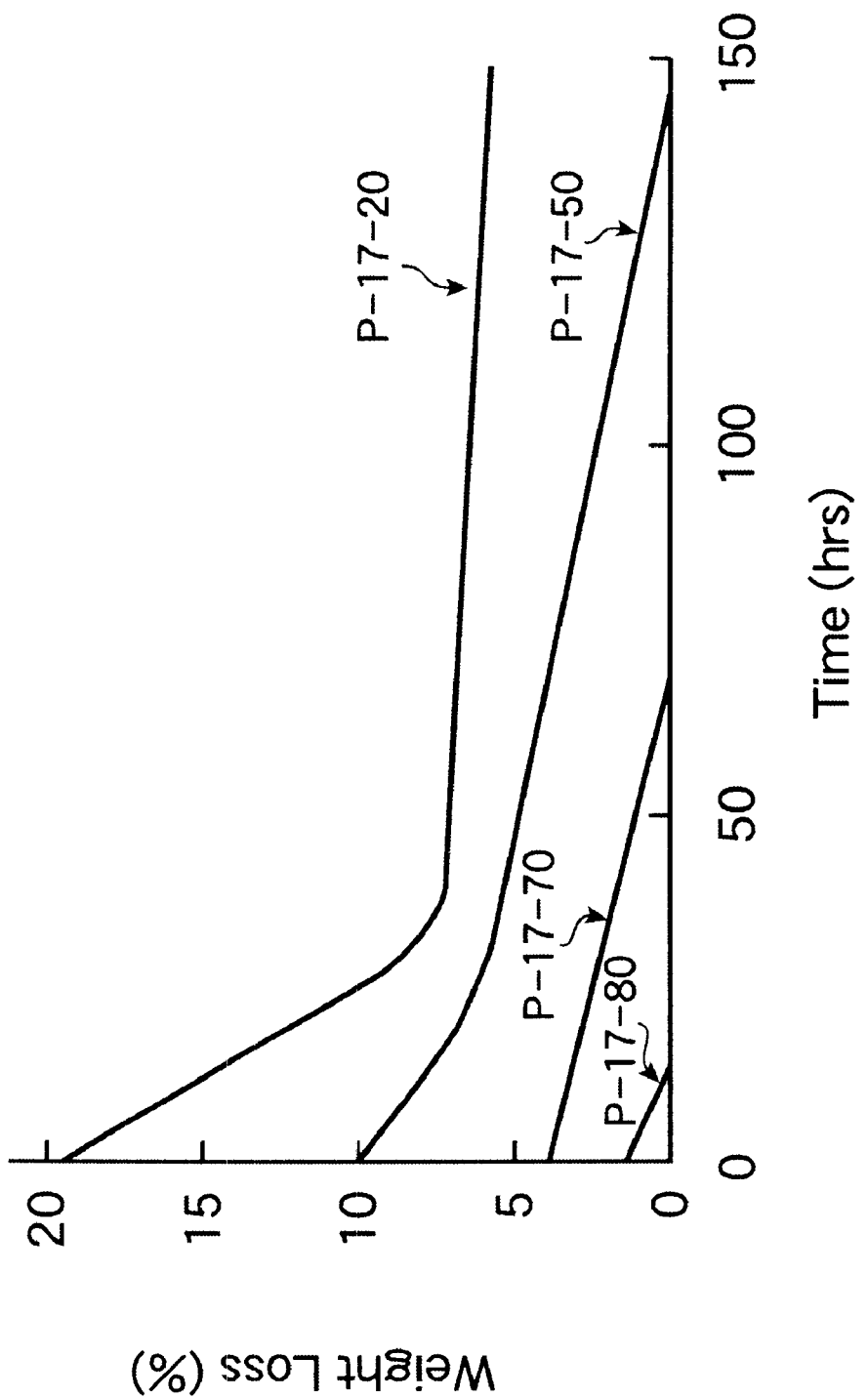
FIG. 2 is a graph showing the relation between the drying time at 120° C. and the residual solvent weight of each cast membrane in Example 8.

Each of the cast membranes obtained was subjected to thermogravimetry using a thermogravimeter (TG-210, manufactured by SeikotInstruments Inc.). Measurements by $^1$H-NMR made on each cast membrane before and after the thermogravimetry revealed that the existence of residual DMAc, used as a solvent in the production, in the membranes before the thermogravimetry. As a typical example, for the cast membrane of P-17-70, the relation between the temperature and the weight loss (%) in the thermogravimetry is shown in FIG. 1. On the assumption that the weight loss of the cast membrane at 150 to 250° C. is due to the solvent DMAc, the relation between the drying time of each cast membrane at 120° C. and the weight of the residual solvent is shown in FIG. 2. It was observed that weight decrease of P-17-50, i.e. the cast membrane made from a polymer having a siloxane component content of 50 wt % or higher, ceased after drying at 120° C. for about 150 hours. However, in the case of the cast membrane comprising a polymer having a siloxane component content of 20 wt % or less, removal of 7 wt % or more of the solvent under the same conditions was difficult. This indicates that the heat drying time under reduced pressure for the cast membrane may vary according to the composition of the polymer.

Thereafter, the cast membranes completely free from solvent and heat-dried under reduced pressure through the thermogravimetry were subjected to analysis by a differential scanning calorimeter (DSC, manufactured by Perkin-Elmer, Pyris measuring device). Every cast membrane showed an endothermic peak due to the solvent around 170° C., indicating the existence of a residual solvent. As a typical Seiko Instruments Inc., TG-210). Analysis by $^1$H-NMR of each film before and after the thermogravimetry revealed the absence of residual DMAc in the films before the thermogravimetry.

Thereafter, analysis by a differential scanning calorimeter (DSC, manufactured by Perkin-Elmer, Pyris measuring device) was carried out on each of the cast membranes confirmed to be completely free from solvent and heat-dried under reduced pressure through the thermogravimetry. None of the heat-molded membranes showed an endothermic peak due to the solvent. As a typical example, the result of measurement by a differential scanning calorimeter made on the film of P-17-70 is shown in FIG. 3 as b.

From the test results obtained above, it can be seen that the heat-molded article of the present invention does not show any existence of residual solvent, even if analyzed by DSC which is higher in sensitivity than $^1$H-NMR and thermogravimetry.

Then, for each of the film made with P-17-70 and, for comparison, a film made in the same manner from PN-17-70 using a hot presser, the degree of coloring was examined using a ultraviolet visible ray spectrophotometer (manufactured by JASCO Corp., Ubest-35).

The film of PN-17-70 in which the terminal amines had not been treated showed an absorption peak in the visible ray region, and therefore coloration was observed. On the other hand, the film made of P-17-70 in which the terminal amines had been treated showed no absorption in the visible ray region, indicating that film is a transparent molded article excellent in heat stability.

Example 10

Using an electronbeam irradiation device (manufactured by Energy Science Inc., Electron Curtain System, Model: CB175-15-180L), the film of P-17-70 fabricated in Example 9 was irradiated with an electron beam at an accelerating voltage of 170 eV and a dose of 0 to 100 Mrad.

Figure 4:
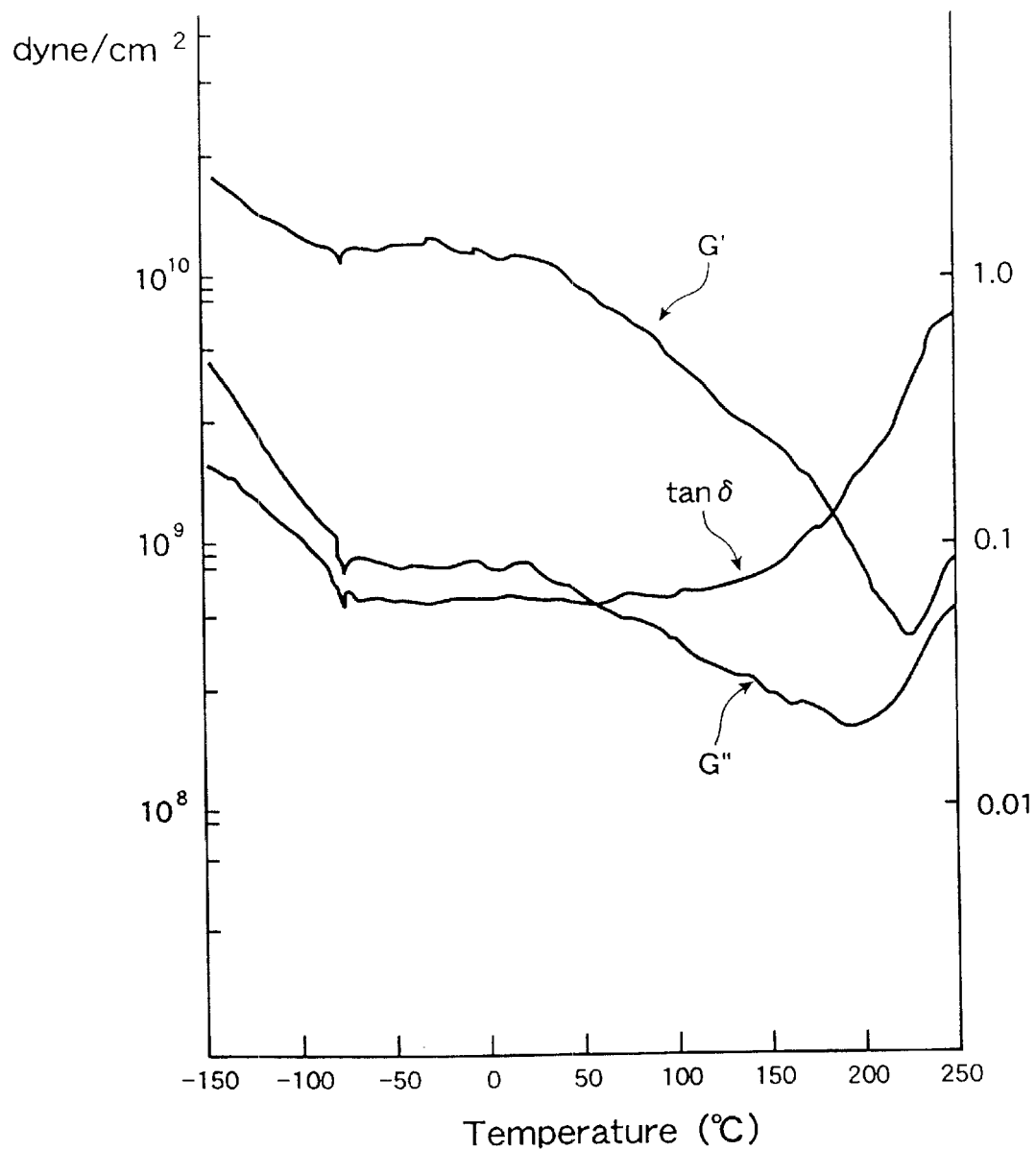
FIG. 4 is a graph showing the dynamic viscoelasticity of the electron beam-irradiated film measured in Example 10.
Figure 5:
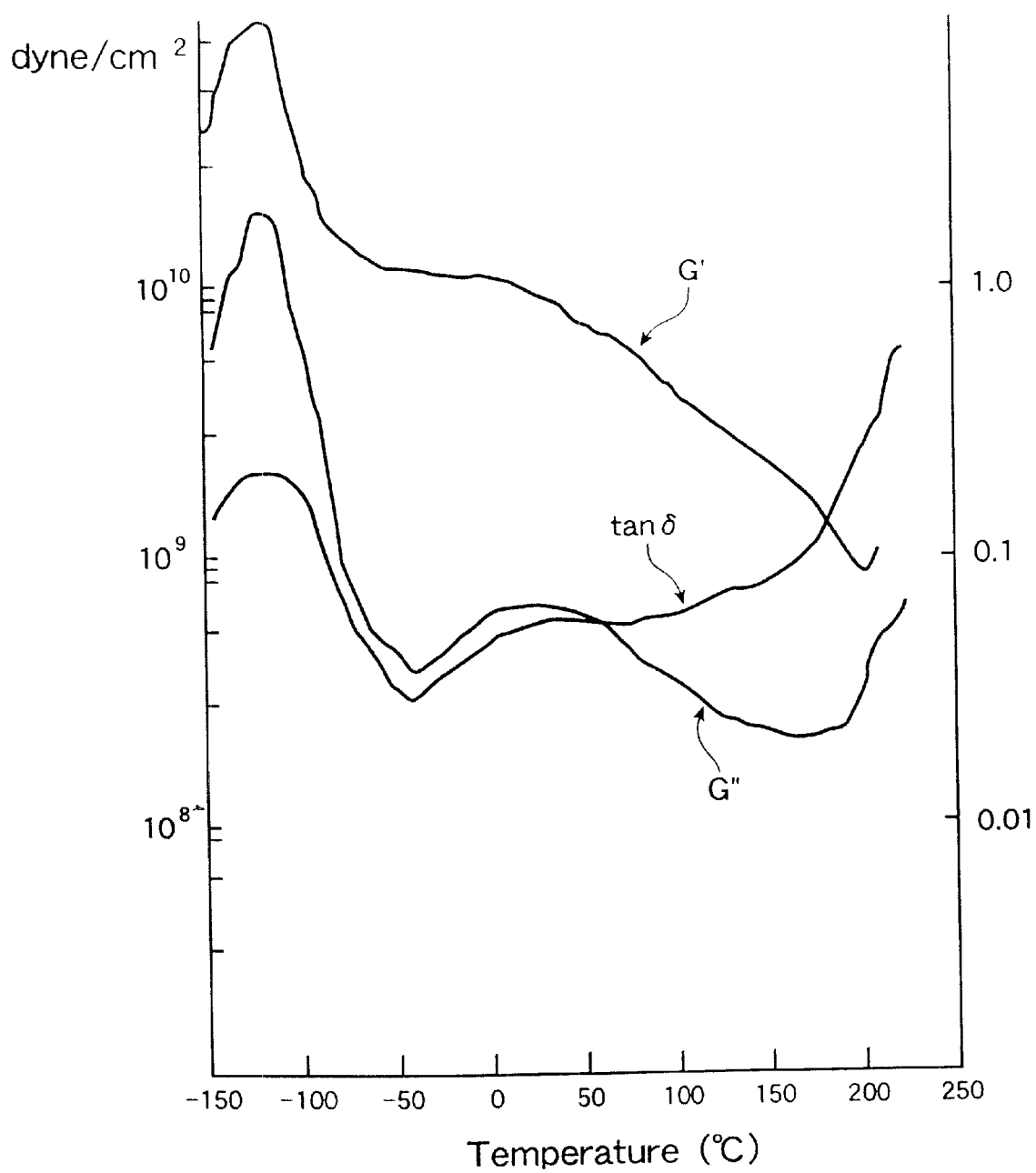
FIG. 5 is a graph showing the dynamic viscoelasticity of the film before the electron beam irradiation measured in Example 10.

Then, the dynamic viscoelasticity of the film after the electron beam irradiation was measured using a Rheovibron (Model: DDV-II-C, manufactured by A&D Orientec Co., Ltd.). The results are shown in FIG. 4. For comparison, the dynamic viscoelasticity of the film of P-17-70 fabricated in Example 9 (electron beam irradiation dose: 0) was also measured in the same manner. The results are shown in FIG. 5. In FIG. 4 and FIG. 5, G' represents the modulus of storage elasticity and G" represents the loss modulus.

From the results shown in FIG. 4 and FIG. 5, it can be seen that the mobility of the siloxane segment shown in FIG. 4 has been suppressed after being crosslinked by the electron beam irradiation.

The TG of the film irradiated with an electron beam (20, 30, 50, and 70 Mrad) was measured using a TMA measuring device (manufactured by Seiko Instruments Inc.). The results are shown in FIG. 6.

Figure 6:
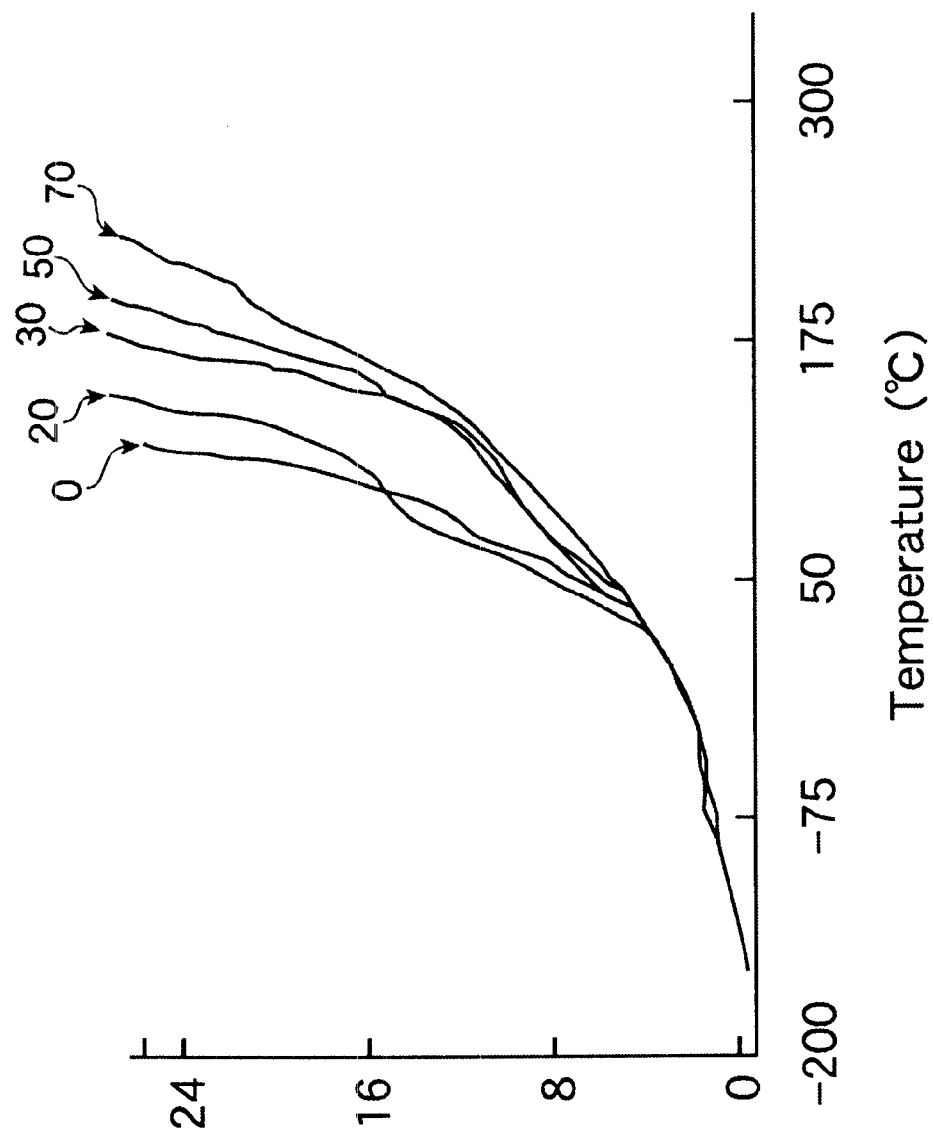
FIG. 6 is a graph showing the measured results of TG of the film irradiated with an electron beam (20, 30, 50, and 70 Mrad) in Example 10.

FIG. 6 shows that, in the range of the irradiation intensity, the softening temperature of the test samples rises as the dose of radiation increases from zero irradiation, indicating a rise in the degree of crosslinking.

From the results obtained above and a comparison of FIG. 4 with FIG. 5, it can be seen that the resonance, observed at −150∼−100° C., of G' and G" representing the mobility of the siloxane segment is reduced by the electron beam irradiation, that is, the mobility of the siloxane segment is restrained. Moreover, from the results shown in FIG. 6, it can be seen that the softening temperature rises as the intensity of irradiation is raised, which results in increase of crosslinking reactions and degree of crosslinking. This effect is also obvious from an increase of the proportion of siloxane.

Example 11

MPC-BMA copolymer (MPC molar fraction: 0.3, number average molecular weight: 80,000) was prepared as 1 wt % ethanol solution, and the solution was casted on an aluminum alloy sheet and dried. On the sheet was placed a fibrous material of P-17-70 prepared in Example 1, and these were molded into a film on a hot plate heated up to 180° C. The film thus obtained was immersed in distilled water and ultrasonically washed. The contact angle of the washed film was measured. Then, the film was rubbed with a spongy scrubbing brush in a neutral detergent to treat the surface. The contact angle of the treated film was measured. The contact angles of the film measured before and after the surface treatment are shown in Table 2. For comparison, the contact angle of a film solely constituted of P-17-70 was also measured in the same manner. The results are shown in Table 2.

TABLE 2

|  | P-17-70 molded article | MPC-BMA-P-17-70 complex | Complex after washing |
|---|---|---|---|
| Angle of advance (deg.) | 105 ± 10 | 5 ± 5 | 5 ± 3 |
| Angle of sweepback (deg.) | 70 ± 10 | 5 ± 3 | 5 ± 2 |

Example 12

MPC-BMA copolymer (MPC molar fraction: 0.3, number average molecular weight: 80,000) was hot-pressed by a hot presser heated to 180° C. to give a transparent plate molded article. The plate molded article and the film fabricated in Example 9 were brought into tight contact with each other and then put in the hot presser at 180° C. with its hot-pressing plate touching the surface of the film (in this case, application of pressure is unnecessary). Taken out of the hot presser after 10 seconds was a laminated composite material, in which the plate molded article and the film had been completely combined together.

An examination by a peel tester resulted in the splitting of the MPC-BMA copolymer layer prior to the delamination of the layers at the interface.

The composite material was immersed in water. The MPC-BMA copolymer layer took in water and swelled. The polydimethylsiloxane/polyamide copolymer layer film fabricated in Example 9 showed almost no change but being largely deformed due to a large swelling of the MPC-BMA copolymer layer. However, even when the deformation had completed, they did not part at the interface.

Example 13

Using a hot presser, from each of P-17-20, P-17-50, P-17-70, P-17-80, P-9-70, and P-30-70 prepared in Examples 1 to 6 was fabricated a film having a thickness of 50 to 100 μm. The oxygen permeability of each of the films thus obtained was measured by the vacuum method. The results are shown in Table 3.

TABLE 3

|  | P-17-20 | P-17-50 | P-17-70 | P-17-80 | P-9-70 | P-30-70 |
|---|---|---|---|---|---|---|
| Oxygen permeability | 13.8 | 75.8 | 157 | 199 | 58.7 | 216 |

Unit: × $10^{-10}$ cm$^3$ (STP) cm/cm$^2$ · sec · mmHg

The results shown in Table 3 indicate that the molded articles made from the copolymer of the present invention have a high oxygen permeability (high Dk value). Accordingly, these molded articles are proved to be useful as materials of ophthalmic lenses such as contact lenses and intraocular lenses or as medical materials that are required to be gas permeable.

Example 14

Using a hot presser, from each of P-17-50, P-17-70 and P-17-80 prepared in Examples 1, 3 and 4 were fabricated five films different in thickness, the thickness ranging from 250 to 800 μm. The oxygen permeability of each of the films thus obtained was measured using an Industrial Products Research Institute-type film oxygen permeability meter (K316, IPI TIPE FILM OXYGEN PERMEABILITY METER, manufactured by Rikaseiki Kogyo Co., Ltd.) with 0.9 wt. % physiological saline at 35° C. The results are shown in Table 4.

TABLE 4

|  | P-17-50 | P-17-70 | P-17-80 |
|---|---|---|---|
| Oxygen permeability (DK) | 301 | 308 | 199 |

Unit: × $10^{-11}$ ml (STP) cm/cm$^2$ · sec · mmHg

The results shown in Table 4 indicate that the molded articles made from the copolymer of the present invention have a high oxygen permeability (high Dk value), proving these molded articles to be useful as ophthalmic lens materials such as contact lenses and intraocular lenses or as medical materials that are required to be gas permeable.

Example 15

Figure 7:
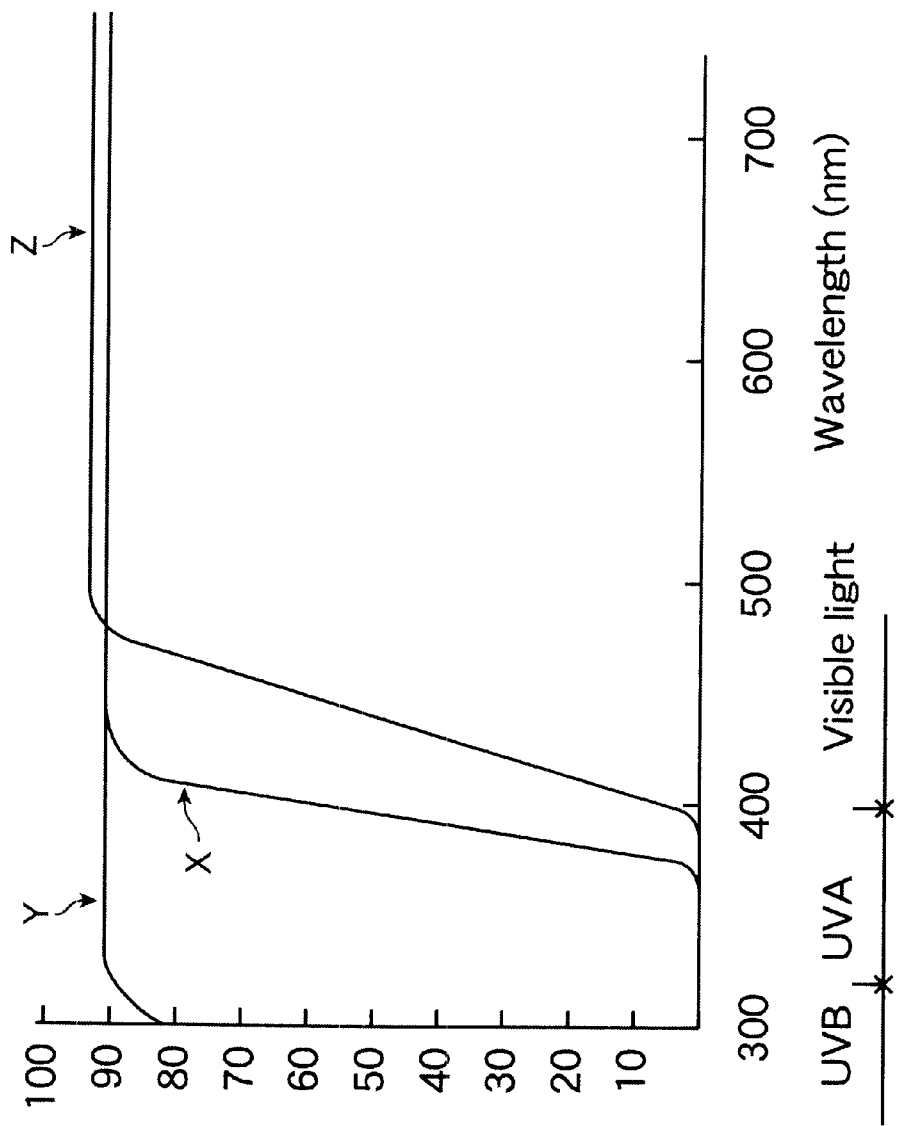
FIG. 7 is a graph showing the ultraviolet and visible ray absorption spectrum measured in Example 15.

Using a hot presser, P-17-70 synthesized in Example 1 was shaped into a film having a thickness of 238 μm. The ultraviolet and visible ray absorption spectrum of the obtained film was measured by a ultraviolet and visible ray spectrophotometer. The result is shown in FIG. 7 as X. For comparison, the result of ultraviolet visible ray spectrometry of a conventional hard contact lens made of poly (methyl methacrylate/silicone) (shown as Y in FIG. 7) and that of a human crystalline lens (shown as Z in FIG. 7) are shown in FIG. 7 together.

From the results shown in FIG. 7, it can be seen that the the molded article (X) molded from the copolymer of the present invention exhibits greater absorption in the ultraviolet ray region than the spectrum (Z) of the transparent tissues of the eyeball, and that the molded article has the ultraviolet ray blocking effect, i.e., effect for protecting the macula lutea from a harmful ray such as ultraviolet rays, and therefore is useful as a medical or ophthalmic material which may be used outdoors.

Example 16

Using a hot presser, each of P-17-50, P-17-70, and P-17-80 prepared in the above-mentioned Examples was shaped into a film having a thickness of 1 mm, and 30 films were made from each polymer. The films thus obtained were piled up to a thickness of 30 mm, and the hardness was determined by a Shore hardness tester. The results are shown in Table 5.

TABLE 5

|  | P-17-50 | P-17-70 | P-17-80 |
| --- | --- | --- | --- |
| Shore hardness | A/90, D/40 | A/85, D/25 | A/45 |

From the results shown in Table 5, it can be seen that the molded article of P-17-50 is useful for fixation members of intraocular lenses, (semi)hard contact lenses, etc., and that each of the molded articles made of P-17-70 and P-17-80 has a useful hardness as a material for soft contact lenses, soft-type intraocular lenses which, in the operation, can be inserted through a small incision.

Example 17

According to "Biomaterials, 13, 113 (1992)", from whole human blood were prepared platelet-rich plasma and platelet-poor plasma, and a platelet suspension having a concentration of $2 \times 10^5/mm^3$ was prepared by mixing them together.

Using a hot presser, each of P-17-50, P-17-70, and P-17-80 prepared in Examples described above was molded into a film having a thickness of 200 μm. For comparison, a Biomer film (manufactured by Ethicon Inc.) and a Silastic film (manufactured by Dow Corning Co.) were used. Each film was punched out in the form a disk of 18 mm in diameter, and the disk film was inserted into a 24-well multiwell, followed by the injection of 0.8 ml of the platelet suspension prepared above. At 37° C., the films were allowed to stand still for 15 minutes to bring platelet into contact with the films. Then the films were taken out of the multiwell and gently washed with aphosphoric acid buffer solution. According to a conventional method, samples for scanning electron microscopic (SEM) observation were prepared. In the scanning electron microscopic observation, the number of platelets adhered to the air-side surface of each film and the state of the platelets were observed using an EMX-SM manufactured by Shimadzu Corp. The results are shown in Table 6.

TABLE 6

| Material | The number of platelets adhered ($/3960\ \mu m^2$) | Form of platelet |
| --- | --- | --- |
| P-17-50 | 1 | No change in the form |
| P-17-70 | 0 | No change in the form |
| P-17-80 | 0 | No change in the form |
| PN-17-70 | 3 | Not much change in the form |
| Silastic | 2 | Not much change in the form |
| Biomer | 6 | Changes in the form with extended pseudopodium |

The results shown in Table 6 indicate that the molded articles made from the copolymer of the present invention have antithrombotic properties and are useful particularly as materials for medical devices having the possibility of coming into contact with blood.

Example 18

The polymer (P-17-70) prepared in Example 1 was put in a metal mold made of SUS316L cut in the shape of a lens, and heat-molded by applying a load of 10 kgf/cm² at 200° C. for 1 minute. As a result, there was provided a colorless, transparent molded article shaped along the mold.

Example 19

Using a metal mold made of SUS316L cut to have the shape corresponding to that of a plate-type intraocular lens, the polymer (P-17-70) prepared in Example 1 was put in an optical member-molding area, and the polymer (P-17-80) prepared in Example 4 in fixation member-molding areas. Under a load of 10 kgf/cm², heat molding was carried out at 200° C. for 1 minute, providing a colorless, transparent molded article shaped along the metal mold, the molded article corresponding to a plate-type intraocular lens. The juncture between two kinds of polymers was even from optical and mechanical viewpoints, and visual inspection of the molded article could not tell where the boundary was.

Example 20

4.0 parts by weight of microcrystalline wax, 3.0 parts by weight of liquid paraffin, 1.0 part of sorbitan sesquioleate, 39.0 parts by weight of decamethylcyclopentasiloxane, 8.0 parts by weight of P-17-50 prepared in Example 3, and 2.0 parts by weight of isopropyl myristate were stirred and dissolved at 70 to 80° C. In the resulting mixture were dispersed 25 parts by weight of kaolin, 15.0 parts by weight of titanium dioxide, and red iron oxide. After deaeration, to the mixture were added flavoring agents in suitable amounts to provide a cosmetic product for skin.

The skin cosmetic product thus obtained was applied to filter paper impregnated with water or squalene, and a dried nylon plate was pressed against the filter paper and vertically shook 10 times. In terms of the density of color, the degree of transference of the skin cosmetic product from the filter paper to the nylon plate after shaking was visually examined by a panel of 10 people. The results are shown in Table 7.

The evaluation was made as follows: no transference: 1 point; slightly transferred: 2 points; considerably transferred: 3 points. The degree of transference was expressed by the average, value of evaluation by all of the panels. Moreover, the sunburn protecting effect of the skin cosmetic product obtained was evaluated by the SPF (Sun Protection Factor) method employing an animal. That is, the skin cosmetic product was applied to, in an amount of 2 μl/cm², a guinea pig the back of which had been depilated using a depilatory cream. After 15 minutes, the cosmetic product-applied area was irradiated with ultraviolet rays using an ultraviolet lamp (manufactured by Toshiba Corp., Model: FL-SE). At the point of time where 24 hours had past since the irradiation, erythemas developed in the cosmetic product-applied area and the cosmetic product non-applied area were observed, and the minimal ultraviolet radiation dosage required to produce slight erythema was found out. SPF was figured out from the minimal ultraviolet ray dosage in accordance with the following equation. The results are shown in Table 8. SPF=(the minimal ultraviolet radiation dosage required to cause the skin to develop etythema in the cosmetic product-applied area)/(the minimal ultraviolet radiation dosage required to cause the skin to develop erythema in the cosmetic product non-applied area).

Comparative Example 2

4.0 parts by weight of microcrystalline wax, 3.0 parts by weight of liquid paraffin, 1.0 part by weight of sorbitan sesquioleate, 47.0 parts by weight of decamethylcyclopentasiloxane, and 2.0 parts by weight of isopropyl myristate were stirred and dissolved at 70 to 80° C. In the resulting mixture were dispersed 25 parts by weight of kaolin, 15.0 parts by weight of titanium oxide, and red iron oxide. After deaeration, to the mixture were added flavor agents in suitable amounts to provide a cosmetic product for skin. The degree of transference and the sunburn protection effect of the skin cosmetic product thus obtained were evaluated in the same manner as in Example 20. The results of the transference test and the sunburn protection effect test are shown in Table 7 and Table 8, respectively.

Example 21

20.0 parts by weight of dimethylpolysiloxane (0.65 cSt), 44.0 parts by weight of dimethylpolysiloxane (2.0 cSt), 15.0 parts by weight of P-17-80 prepared in Example 4, and 5.0 parts by weight of $(CH_3)_3SiO/SiO_2/(CH_3)_2SiO=2.4/1.6/1.0$ (molar ratio) were stirred and dissolved at 70 to 80° C. 6.0 parts by weight of glycerol triisostearate and 10 parts by weight of roller-processed Red No. 226 were added to the resulting mixture and dispersed therein. After deaeration, to the dispersion were added flavor agents in suitable amounts to prepare liquid rouge. The degree of transference of the liquid rouge thus obtained was examined in the same manner as in Example 20. The results are shown in Table 7.

Comparative Example 3

20.0 parts by weight of dimethylpolysiloxane (0.65 cSt), 44.0 parts by weight of dimethylpolysiloxane (2.0 cSt), 15.0 parts by weight of high-molecular weight dimethylpolysiloxane, and 5.0parts by weight of $(CH_3)_3SiO/SiO_2/(CH_3)_2SiO=2.4/1.6/1.0$ (molar ratio) were stirred and dissolved at 70 to 80° C. 6.0 parts by weight of glycerol triisostearate and 10.0 parts by weight of roller-processed Red No. 226 were added to the resulting mixture and dispersed therein. After deaeration, to the dispersion were added suitable amounts of flavor agents to prepare liquid rouge. The degree of transference of the rouge thus obtained was examined in the same manner as in Example 20. The results are shown in Table 7.

TABLE 7

|  | Water | Squalene |
| --- | --- | --- |
| Example 20 | 0.8 points | 0.8 points |
| Comp. Example 2 | 2.0 points | 3.0 points |
| Example 21 | 0.7 points | 0.8 points |
| Comp. Example 3 | 1.5 points | 1.8 points |

TABLE 8

|  | SPF |
| --- | --- |
| Example 20 | 20.5 |
| Comp. Example 2 | 8.3 |

From the results shown in Table 7, it can be seen that both the skin cosmetic product of Example 20 and the rouge of Example 21 are superior in water resistance and oil resistance to those in Comparative Examples. Moreover, all of the products of Examples felt refreshing on the skin than those of Comparative Examples. From the results shown in Table 8, it was found that the skin cosmetic product of Example 20 was much excellent in ultraviolet ray blocking properties than that of Comparative Example 2.

Example 22

25 g of P-17-50 prepared in Example 3, 0.3 g of a nonionic urethane-associated thickener (manufactured by Servo Delden B.V., SER AD FX 1100), 1 g of a pigment, and 73.7 g of water were mixed together to provide nail varnish.

The nail varnish thus obtained was highly water-resistant, and the coating layer obtained by applying the varnish onto nail was not cracked and kept its perfect condition even when subjected to stirring in water for 1 hour. The coat obtained did not peel off and properly adhered to the keratin in the nail without tackiness, proving resistant to scratching. Accordingly, this nail varnish can readily be applied onto the nail and exhibit a significantly good gloss and durability.

Example 23

11.8 g of triethanolamine stearate, 5 g of bee wax, 3 g of carnauba wax, and 1 g of paraffin were mixed together, heated up to 85° C., and admixed with 5 g of black iron oxide to give a mixture. Then, 2 g of gum Arabia and 1.2 g of hydroxyethylcellulose (manufactured by Amercol, Cellosize QP) were added to 46 g of pharmaceutical water heated to 85° C. While treating with a homogenizer, to the resulting mixture was added the mixture first prepared, followed by cooling to 30° C. Lastly, 25 g of P-17-70 prepared in Example 1 was added to the mixture and stirred to provide a mascara composition.

Example 24

A shampoo was prepared from 5 g of P-17-70 prepared in Example 1, 15 g of sodium laurylether sulfate, 3 g of a 32% aqueous solution of cocoylbetaine (manufactured by Chimex, Chimexane HC), trace amounts of a flavor agent and a preservative, and 77 g of water.

Example 25

A hair styling lotion was prepared from 5 g of P-17-70 prepared in Example 1, trace amounts of a flavor agent, a dye, and a preservative, and 95 g of water. Application of this lotion to the shampooed hair gave a good shape-retention capability thereto, and the hair became excellently glossy.

Example 26

A hairspray liquid was prepared from 3 g of P-17-70 prepared in Example 1, trace amounts of a flavor agent, a dye, and a preservative, and 97 g of water. The hair spray liquid was charged into a pump flask and then sprayed over hair. The hair was given a good shape-retention capability and became excellently glossy.

Example 27

As can be seen from FIG. 7, the P-17-70 film fabricated in Example 15 shows excellent transparency in a wavelength region longer than 380 nm, so that it is useful for the core layer of an optical fiber. The refractive index of the film, measured at 25° C. using the sodium D line, was found to be 1.49. Further, using P-17-70 prepared in Example 1, a 80 μm-thick film was formed on fused quartz glass according to the casting method. The propagation loss of the film, measured using a He—Ne-laser beam (wavelength=632.8 nm), was found to be 0.8 dB/cm. The results obtained above prove that the film is excellent in optical characteristics and useful as an optical fiber material.

Example 28

0.005 mol of 3,4'-DAPE, 0.0025 mol (molecular weight: 1,680) of PDMS-dNH$_2$, and 0.015 mol of triethylamine were dissolved in 25 ml of a reaction solvent (DMAc:THF= 1:2) to prepare a reaction solution (a). 0.0075 mol of IPC was dissolved in 25 ml of the same reaction solvent to prepare a reaction solution (b). 0.00075 mol of IPC was dissolved in 1 ml of the same reaction solvent to prepare a reaction solution (c). 0.0008 ml of ethanol was dissolved in 1 ml of the same reaction solvent to prepare a reaction solution (d).

The reaction solution (a) was poured into a flask, and the reaction solution (b) into a dropping funnel equipped with a cooling medium system. With the dropping funnel and the flask kept at 0° C. by a cooling medium, the reaction solution (b) was added to the reaction solution (a) dropwise with stirring. After 1 hour, to the resulting mixture was added the reaction solution (c). After another 5 minutes, 0.0015 mol of triethylamine was added. At the point of time where another 5 minutes had passed, to the mixture was added the reaction solution (d). Then, the cooling bath was taken away and the mixture was kept stirred for another 50 minutes.

The solution thus obtained was filtered through 5C filter paper, and the polymer solution obtained was subjected to reprecipitation using 1 L of purified water. A precipitate was taken out of the solution, dried at 60° C. overnight, re-dissolved in 60 g of THF, and subjected to reprecipitation again using 1 L of a solution [purified water:methanol 1:1 (volume ratio)].

The precipitate obtained was dried again at 60° overnight, re-dissolved in 50 g of THF, and filtered by a pressure filter equipped with a 0.5 μm-membrane filter made of polytetrafluoroethylene. Further, the solution was subjected to reprecipitation in 1 L of a solution (purified water:methanol= 1:1 (volume ratio)), dried at 60° C. overnight, and dried at 120° C. for 4 hours to provide a polydimethylsiloxane/polyamide copolymer (hereinafter, abbreviated as PAS).

Example 29

A spacer for pressing (a 500 μm-thick metal piece with a hole of 5 cm×5 cm) was placed on an aluminum pressing sheet washed with acetone. Inside the hole of the spacer, 1.25 to 1.40 g of PAS prepared in Example 28 was placed, and the hole was covered with the washed aluminum sheet. This test sample was set on the stage of a presser (manufactured by Toyo Seiki Seisaku-sho, Ltd., tradename "Mini Test Press-10") and allowed to stand at 200° C. for 10 minutes. Then, with the temperature kept at 200° C., a pressure of 10 MPa was applied to the test sample. After having been allowed to stand for 10 minutes, the test sample was cooled to room temperature. With a cutter, the PAS sheet thus obtained was cut into pieces of 15 mm×50 mm to prepare PAS test pieces that would be subjected to a variety of surface treatments.

Example 30

One of the PAS test pieces prepared in Example 29 was hung within a 50-ml sample tube, and 90% of the mouth of the sample tube was closed by utilizing an inner lid. Oxygen was supplied to an ozone generator (manufactured by Nippon Ozone Co., Ltd., Model: 0-3-2,) at a rate of 0.3 L/min. and ozone was generated under the condition of 100 V. The ozone generated by the generator was introduced to the aforementioned sample tube through a tube made of vinyl chloride. Under normal pressure, ozone treatment was carried out at an ordinary temperature and pressure for 30 minutes to prepare an ozone-treated PAS test piece.

Example 31

One of the PAS test pieces prepared in Example 29 was attached to a Teflon sheet (thickness: 0.2 mm, approximately 20 cm×20 cm) via a double-faced adhesive tape. Each sheet was placed on the belt conveyer of a corona discharge treatment device (manufactured by Kasuga Denki, K.K., Model: AGI-021S) to perform corona discharge treatment on the PAS test pieces for preparing a corona discharge-treated PAS test piece. The speed of the belt conveyer was set a 74.1 mm/s, and the treatment was carried out 5 times at a discharging output of 150 W, and one time at 300 W.

Example 32

One of the PAS test pieces prepared in Example 29 was placed within an atmospheric pressure plasma treatment device, and helium gas was passed therethrough for 15 minutes. Then, the test piece was irradiated with helium plasma for 5 minutes under the conditions of 1.6 kV and 20 kHz, to prepare an ambient pressure plasma-treated PAS test piece.

Example 33

The ambient pressure plasma-treated PAS test piece prepared in Example 32 was immersed in polyethylene glycol (Mw=200, OH-terminated) (hereinafter, abbreviated as PEG) for 10 minutes and brought into contact with helium gas for 10 to 20 minutes. The test piece was immersed in PEG heated up to 110° C. again and, with helium gas kept flowing at a rate of 3,000 sec/cm$^3$, the test piece was irradiated with plasma for 5 minutes under the conditions of 1.6 kV and 20 kHz. Further, helium gas was passed for another 5 minutes to prepare a PEG-treated PAS test piece.

Example 34

The PAS test piece prepared in Example 29 was placed on the electrode of a plasma treatment device (manufactured by SAMCO, Model: PD-2), and air was supplied in an amount such that the pressure became 0.1 Torr. Plasma was generated by applying a high-frequency voltage at 50 W for 10 minutes, and the test piece was plasma-treated, to prepare a reduced pressure plasma-treated PAS test piece.

Example 35

The PAS test piece prepared in Example 29 was immersed in a 5% aqueous solution of MPC-SMA copolymer (compositional molar ratio: 9:1, molecular weight: 100,000) (hereinafter, abbreviated as PMS) at room temperature for 3 hours and naturally dried to prepare a PMS-absorbed PAS test piece. The test piece was not rinsed.

Example 36

The test piece prepared in Example 29 was placed on a hot plate heated up to 100° C. A glass sprayer for TLC dyeing was connected to a compressor. A 5 wt. % ethanol solution of MPC-BMA copolymer (compositional molar ratio: 3:7, molecular weight: 280,000) (hereinafter, abbreviated as PMB) was sprayed over the test piece for about 30 seconds, to prepare a PMB-coated PAS test piece.

Example 37

MPC-allylamine (compositional molar ratio: 99:1, Mw: 1,000,000, Mw/Mn=5.7) (hereinafter, abbreviated as PMA) was dissolved in 40 ml of water. The pH of the resulting mixture was adjusted to about 4 with the use of 0.1N—HCl, followed by the addition of a water-soluble carbodimide in an amount 10 times the molar quantity of the amine in the PMA added. Thereafter, three reduced pressure plasma-treated PAS test pieces were put in the solution and allowed to stand overnight. These test pieces were rinsed with portions of approximately 50 ml of purified water 10 times and naturally dried to prepare PMA-fixed PAS test pieces.

Reference Example 1

The treated PAS test pieces prepared in Examples 29 to 37 were subjected to X-ray photoelectron spectroscopic examination (XPS) by a ESCA-3300 manufactured by Shimadzu Corp. The measurement was carried out under standard conditions with 8 times of accumulation. The results are shown in Table 9.

The results confirmed that the chemical composition of the surface of the PAS test piece was modified by the treatments. Particularly, it was found that coating of the test piece with the MPC polymer results in appearance of the phosphorus atoms due to MPC on the surface, and reduction of the amount of the nitrogen atoms due to PAS.

Reference Example 2

For each of the PAS test pieces treated in Examples 29 to 37, the dynamic contact angle was measured using a DCA-20 manufactured by Orientec Co., Ltd. The measurement was conducted under the conditions of an immersion rate of 10 mm/min., an immersion length of 30 mm, and a temperature of 25° C.

The charts obtained included straightly-lined ones and jaggy-lined ones. The variety of lines may be due to difference in reliability of data. Therefore, the reliability of the data was graded by the following criteria. Straightly-lined: ○, Jaggy-lined: X, and Intermediate: Δ. Together with the dynamic contact angles, the results are shown in Table 10. In jaggy-lined charts, the contact angle was figured out utilizing a straightly-lined part. In the table, $\theta_A$ represents the angle of advance, $\theta_R$ represents the angle of sweepback, and $\Delta\theta$ represents the difference between the angle of advance and the angle of sweepback.

TABLE 10

| | | Reliability | θ A | θ R | Δ θ |
|---|---|---|---|---|---|
| Ex. 29 | RUN 1 | ○ | 105 | 76 | 29 |
| | RUN 2 | ○ | 105 | 75 | 30 |
| Ex. 30 | RUN 1 | ○ | 115 | 49 | 66 |
| | RUN 2 | ○ | 108 | 51 | 56 |
| Ex. 31 | RUN 1 | Δ | 92 | 61 | 32 |
| | RUN 2 | Δ | 98 | 63 | 35 |
| Ex. 32 | RUN 1 | ○ | 98 | 66 | 32 |
| | RUN 2 | ○ | 101 | 77 | 25 |
| Ex. 33 | RUN 1 | Δ | 62 | 42 | 21 |
| | RUN 2 | Δ | 62 | 41 | 21 |
| Ex. 34 | RUN 1 | ○ | 57 | 42 | 15 |
| | RUN 2 | Δ | 49 | 38 | 11 |

TABLE 9

| | | Cl (1S$_1$) | Cl (1S$_2$) | Cl (1S$_3$) | N (1S$_1$) | O (1S$_1$) | Si (2P) | P (2P) |
|---|---|---|---|---|---|---|---|---|
| Ex. 29 | RUN 1 | 47.46 | 7.11 | 1.66 | 1.77 | 20.23 | 21.76 | Not measured |
| | RUN 2 | 47.68 | 6.68 | 1.70 | 1.43 | 20.55 | 21.96 | Not measured |
| Ex. 30 | RUN 1 | 39.23 | 10.35 | 2.79 | 1.62 | 23.30 | 22.60 | 0.10 |
| Ex. 31 | RUN 1 | 32.36 | 5.72 | 1.21 | 1.04 | 32.58 | 27.08 | 0.02 |
| | RUN 2 | 33.35 | 4.89 | 2.15 | 0.92 | 32.46 | 26.24 | 0.00 |
| Ex. 32 | RUN 1 | 39.89 | 6.70 | 1.11 | 1.68 | 28.21 | 22.40 | Not measured |
| | RUN 2 | 35.74 | 8.44 | 2.62 | 1.56 | 28.26 | 23.38 | Not measured |
| Ex. 33 | RUN 1 | 26.70 | 12.47 | 0.24 | 0.70 | 35.26 | 24.64 | Not measured |
| | RUN 2 | 28.69 | 12.68 | 1.46 | 0.67 | 34.54 | 21.96 | Not measured |
| Ex. 34 | RUN 1 | 17.85 | 12.06 | 9.42 | 5.70 | 41.08 | 13.88 | Not measured |
| | RUN 2 | 26.14 | 10.93 | 5.89 | 3.70 | 35.12 | 18.22 | Not measured |
| Ex. 35 | RUN 1 | 40.96 | 10.71 | 3.29 | 1.53 | 21.49 | 21.78 | 0.23 |
| | RUN 2 | 43.17 | 10.26 | 1.36 | 1.52 | 21.48 | 21.93 | 0.27 |
| Ex. 36 | RUN 1 | 45.21 | 15.23 | 4.62 | 1.26 | 21.83 | 10.30 | 1.54 |
| | RUN 2 | 40.28 | 18.66 | 2.92 | 1.65 | 22.02 | 13.28 | 1.20 |
| Ex. 37 | RUN 1 | 32.65 | 14.44 | 0.51 | 0.75 | 27.73 | 22.97 | 0.94 |
| | RUN 2 | 37.03 | 9.31 | 0.51 | 0.56 | 27.09 | 24.69 | 0.82 |

TABLE 10-continued

|  |  | Reliability | θ A | θ R | Δ θ |
|---|---|---|---|---|---|
| Ex. 35 | RUN 1 | ○ | 104 | 49 | 55 |
|  | RUN 2 | ○ | 100 | 52 | 48 |
| Ex. 36 | RUN 1 | ○ | 106 | 25 | 81 |
|  | RUN 2 | ○ | 106 | 51 | 56 |
| Ex. 37 | RUN 1 | ○Δ | 33 | 27 | 6 |
|  | RUN 2 | ○Δ | 52 | 28 | 24 |

As a result, the contact angle of the materials with water was changed by any of the surface treatment, indicating that the composition of the surface underwent certain changes.

Reference Example 3

To each of the treated PAS test pieces prepared in Example 31 (treatment II), Example 36, and Example 37 was applied a sufficient amount of a liquid dishwashing detergent (trade name Family Fresh, manufactured by Kao Corporation), and each piece was strongly rubbed with a thumb and an index finger. Thereafter, each test piece was washed with tap water, rinsed with purified water, and dried to give a sample which had been abrasively washed with a detergent. The dynamic contact angle of each of the washed samples thus obtained was determined in the same manner as in Reference Example 2 to evaluate its wettability. The results are shown in Table 11.

TABLE 11

|  |  | Reliability | θ A | θ R | Δ θ |
|---|---|---|---|---|---|
| Example 31 | RUN 1 | ○Δ | 107 | 71 | 35 |
|  | RUN 2 | ○Δ | 104 | 79 | 25 |
| Example 36 | RUN 1 | ○ | 103 | 47 | 57 |
| Example 37 | RUN 1 | Δ | 66 | 38 | 28 |

As seen from Table 11, the contact angle of the test piece of Example 30 was increased, i.e., the hydrophilicity thereof was decreased. However, the test pieces of Examples 36 and 37 keeps the contact angle to the same extent as the pre-washed samples, regardless of the fact that they underwent a severe treatment. As to the MPC polymer absorbed by the test piece, it has been known that, even without rubbing, MPC polymer is peeled off by being immersed in sodium dodecyl sulfate, a surfactant. Accordingly, the test pieces of Examples 36 and 37 were found to be coated with the MPC polymer with considerably high durability.

Example 38

3,4'-DAPE (0.005 mol), 4.20 g (0.0025 mol) of PDMS-NH$_2$ (Mw: 1,680), and 1.52 g (0.0015 mol) of triethylamine were weighed out, put in a 110-ml screw tube, dissolved in 25 ml of a mixed solvent of DMAC and THF (1:2), and kept under ice cooling. 1.52 g (0.0075 mol) of IPC was weighed out, put in another container, dissolved in 25 ml of a mixed solvent of DMAc and THF (1:2), poured into the screw tube mentioned above, and stirred for 30 minutes. The temperature of the resulting mixture was brought back to room temperature and the mixture was stirred for another 30 minutes. The mixture was admixed with 59 mg (0.00075 mol) of acetyl chloride and 76 mg (0.00075 mol) of triethylamine and stirred for 30 minutes. After having been admixed with 35 mg (0.00075 mol) of ethanol, the mixture was stirred for 30 minutes. Then, the mixture was twice subjected to reprecipitation from 1 L of water twice, and the PAS thus obtained was vacuum-dried to give a polymer.

The yield was calculated by measuring the dry weight of the polymer obtained.

The molecular weight was determined using a GPC device. The concentration of the sample was set at approximately 4 mg/ml, 20 μl of which was injected per shot. Employed as the eluent was a solvent prepared by adding 10 mmol of lithium chloride to a mixture of DMAc and MEK [3:10 (volume ratio)]. As the columns for the GPC device, two Mixed-B manufactured by PL Laboratories were employed. Using PEG as the reference material, the determination of molecular weight was carried out under the conditions of 40° C. and a flow rate of 1.00 ml/min.

Further, 0.4 g of the polymer obtained was pressed under the conditions of 180° C. and 10 MPa. The transparency of the film thus obtained was visually examined and graded by the following criteria: Highly transparent: ○, Cloudy and not transparent: X, slightly cloudy but substantially transparent: Δ. The degree of yellowing (color change) of the hot-pressed film after one month was visually examined and graded by the following criteria: No yellowing observed: ○, Yellowing observed: X. The results are shown in Table 12.

Examples 39 to 50

Except that the polymerization solvent was changed to a solvent specified in Table 12, a copolymer and a hot-pressed film were prepared and evaluated in the same manner as in Example 38. The results are shown in Table 12.

Comparative Example 4

100.12 g (0.5 mol) of 3,4'-DAPE, 161.02 g (1.2 mol) of triethylamine hydrochloride, and 101.19 g (1 mol) of triethylamine were dissolved in 2130.49 g of chloroform. Under ice cooling, to the solution thus obtained was added a solution prepared by dissolving 152.265 g (0.75 mol) of IPC in 2498.7 g of chloroform, and the mixture was stirred for 1 hour. Thereafter, to the mixture was added a solution prepared by dissolving 420 g (0.25 mol) of PDMS-NH$_2$ (Mw: 1,680) and 50.595 g (0.5 mol) of triethylamine in 1332.96 g of chloroform, and the resulting mixture was stirred for another 1 hour. The mixture was twice subjected to reprecipitation from 30 L of a mixed solvent of methanol and ethanol, and PAS thus obtained was vacuum-dried to give a polymer. A hot-pressed film was made from the polymer and evaluated in the same manner as in Example 38. The results are shown in Table 12.

TABLE 12

|  | Solvent (Ratio) | Yield (%) | Molecular weight measurement (GPC) | | Hot pressed film | | |
|---|---|---|---|---|---|---|---|
|  |  |  | Mw × 10$^4$ | Mw/Mn | Moldability | Transparency | Yellowing |
| Ex. 38 | DMAc/THF (1/2) | 83 | 3.36 | 2.37 | ○ | Δ | ○ |
| Ex. 39 | CH$_3$CN/THF (1/2) | 90 | 5.61 | 1.91 | ○ | Δ | ○ |
| Ex. 40 | CH$_3$CN/diglyme (1/2) | 83 | 4.31 | 1.85 | ○ | ○ | ○ |

TABLE 12-continued

|  | Solvent (Ratio) | Yield (%) | Molecular weight measurement (GPC) | | Hot pressed film | | |
|---|---|---|---|---|---|---|---|
|  |  |  | Mw × 10⁴ | Mw/Mn | Moldability | Transparency | Yellowing |
| Ex. 41 | CH₃CN/dioxane (1/2) | 71 | 3.50 | 1.70 | ○ | Δ | ○ |
| Ex. 42 | DMAc/THF (1/9) | 100 | 2.84 | 2.09 | Δ | ○ | ○ |
| Ex. 43 | DMAc/THF (1/4) | 97 | 2.90 | 2.32 | Δ | ○ | ○ |
| Ex. 44 | DMAc/THF (1/2) | 94 | 2.42 | 2.86 | ○ | ○ | ○ |
| Ex. 45 | DMAc/THF (1/1) | 92 | 1.97 | 2.02 | ○ | ○ | ○ |
| Ex. 46 | DMAc/DME (1/2) | 94 | 2.17 | 1.93 | ○ | ○ | ○ |
| Ex. 47 | DMAc/diglyme (1/2) | 76 | 2.48 | 1.91 | Δ | Δ | ○ |
| Ex. 48 | DMAc/dioxane (1/2) | 90 | 2.00 | 2.21 | Δ | Δ | ○ |
| Ex. 49 | CH₃CN/THF (1/2) | 99 | 2.68 | 2.20 | ○ | ○ | ○ |
| Ex. 50 | CH₃CN/THF (1/2) | 91 | 4.23 | 2.72 | ○ | Δ | ○ |
| Comp. Ex. 4 | chloroform/thriethylamine hydrochloride | 53.2 | 15.9 | 3.54 | x | x | x |

What is claimed is:

1. A polydialkylsiloxane/polyamide copolymer obtained by polymerizing:

an amino compound represented by formula (I) having amino groups at both ends and a dialkylsiloxane chain:

$$H_2N-R^1-(Si(R^2)(R^3)-O)n^1-Si(R^2)(R^3)-R^1-NH_2 \quad (1)$$

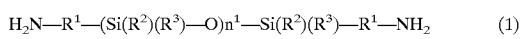

wherein $R^1$ represents a divalent organic group having 1 to 10 carbon atoms, $R^2$ and $R^3$ are the same or different, each representing an organic group having 1 to 7 carbon atoms, and $n^1$ denotes an integer of 5 to 200, a diamino compound represented by formula (2):

$$H_2N-A^1-NH_2 \quad (2)$$

wherein $A^1$ represents a divalent organic group having 1 to 20 carbon atoms, and a dicarboxylic acid chloride represented by the formula (3):

$$ClCO-B-COCl \quad (3)$$

wherein B represents a divalent organic group having 1 to 20 carbon atoms;

to form a polydialkylsiloxane/polyamide copolymer (A) containing amino groups at the ends thereof and having a ratio of $-R^1-(Si(R^2)(R^3)-O)n^1-Si(R^2)(R^3)-R^1$ to $A^1$ within the range of 1:0.01~100; and subsequently reacting the copolymer (A) with an acyl chloride having 2 to 8 carbon atoms.

2. The polydialkylsiloxane/polyamide copolymer according to claim 1, wherein the polymerization reaction of: the amino compound represented by formula (1), the diamino compound represented by formula (2), and the dicarboxylic acid chloride represented by formula (3), is performed in a solvent selected from the group consisting of: dimethylformamide, dimethylacetamide, tetrahydrofuran, dioxane, acetonitrile, dimethoxyethane, acetone, methyl ethyl ketone, diglyme, methyl acetate, ethyl acetate, and mixtures thereof, at a temperature of from −80° C. to 60° C.; wherein said polydialkylsiloxane/polyamide copolymer is purified using a solution selected from the group consisting of: alcohols having 1 to 8 carbon atoms, water, and mixtures thereof; and wherein said purification is performed after copolymer (A) is reacted with said acyl chloride having 2–8 carbon atoms.

3. A cosmetic composition comprising the polydialkylsiloxane/polyamide copolymer of claim 1.

4. An electronic material comprising the polydialkylsiloxane/polyamide copolymer of claim 1.

5. A molded article obtained by molding a material for molding containing the polydialkylsiloxane/polyamide copolymer according to claim 1.

6. The molded article according to claim 5, wherein said molding is heat-molding, said material comprises a solvent, and wherein said solvent is substantially eliminated as a result of molding.

7. The molded article according to claim 5, which is obtained by, after molding, forming crosslinking by energy beam irradiation.

8. The molded article according to claim 5, wherein the molded article comprises at least one surface, and said article is obtained by chemically modifying a surface thereof after molding.

9. The molded article according to claim 5, wherein the molded article comprises at least one surface, and wherein said surface is provided with, after molding, a membrane containing a copolymer comprising hydrophilic monomer units and hydrophobic monomer units, wherein said monomer units are present in a ratio of hydrophilic monomer units to hydrophobic monomer units of 1:0.01~100.

10. The molded article according to claim 5, wherein the molded article comprises at least one surface, and wherein said surface, after molding, is tightly fixed to a molded article containing a copolymer comprising hydrophilic monomer units and hydrophobic monomer units, wherein said monomer units are present in a ratio of hydrophilic monomer units to hydrophobic monomer units of 1:0.01~100.

11. An ophthalmic material comprising a molded article according to claim 5.

12. A medical material comprising a molded article according to claim 5.

13. An electronic material comprising the molded article according to claim 5.

14. A polydialkylsiloxane/polyamide copolymer obtained by polymerizing:

an amino compound represented by formula (I) having amino groups at both ends and a dialkylsiloxane chain:

$$H_2N-R^1-(Si(R^2)(R^3)-O)n^1-Si(R^2)(R^3)-R^1-NH_2 \quad (1)$$

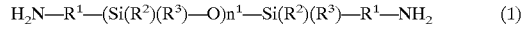

wherein $R^1$ represents a divalent organic group having 1 to 10 carbon atoms, $R^2$ and $R^3$ are the same or different, each representing an organic group having 1 to 7 carbon atoms, and $n^1$ denotes an integer of 5 to 200, a diamino compound represented by formula (2):

$$H_2N\text{—}A^1\text{—}NH_2 \quad (2)$$

wherein $A^1$ represents a divalent organic group having 1 to 20 carbon atoms, and a dicarboxylic acid chloride represented by the formula (3):

$$ClCO\text{—}B\text{—}COCl \quad (3)$$

wherein B represents a divalent organic group having 1 to 20 carbon atoms;

to form a polydialkylsiloxane/polyamide copolymer (A) containing amino groups at the ends thereof and having a ratio of —$R^1$—(Si($R^2$)($R^3$)—O)$n^1$—Si($R^2$)($R^3$)—$R^1$ to $A^1$ within the range of 1:0.01~100; subsequently reacting the copolymer (A) with a dicarboxylic acid chloride represented by formula (3) to form a reaction product; and subsequently reacting said reaction product with a compound selected from the group consisting of: a monovalent hydroxyl group-containing compound having 1 to 8 carbon atoms, a monovalent amino group-containing compound having 1 to 8 carbon atoms, and mixtures thereof.

15. The polydialkylsiloxane/polyamide copolymer according to claim 14, wherein the polymerization reaction of: the amino compound represented by formula (1), the diamino compound represented by formula (2), and the dicarboxylic acid chloride represented by formula (3), is performed in a solvent selected from the group consisting of: dimethylformamide, dimethylacetamide, tetrahydrofuran, dioxane, acetonitrile, dimethoxyethane, acetone, methyl ethyl ketone, diglyme, methyl acetate, ethyl acetate, and mixtures thereof, at a temperature of from −80° C. to 60° C.; wherein said polydialkylsiloxane/polyamide copolymer is purified using a solution selected form the group consisting of: alcohols having 1 to 8 carbon atoms, water, and mixtures thereof; and wherein said purification is performed after the subsequent steps of reacting copolymer (A) with dicarboxylic acid chloride to form a reaction product and reacting said reaction product with a compound selected from the group consisting of: a monovalent hydroxyl group-containing compound having 1 to 8 carbon atoms, a monovalent amino group-containing compound having 1 to 8 carbon atoms, and mixtures thereof.

16. A cosmetic composition comprising the polydialkylsiloxane/polyamide copolymer of claim 14.

17. An electronic material comprising the polydialkylsiloxane/polyamide copolymer of claim 14.

18. A molded article obtained by molding a material for molding containing the polydialkylsiloxane/polyamide copolymer according to claim 14.

19. The molded article according to claim 18, wherein said molding is heat-molding, said material comprises a solvent, and wherein said solvent is substantially eliminated as a result of molding.

20. The molded article according to claim 18, which is obtained by, after molding, forming crosslinking by energy beam irradiation.

21. The molded article according to claim 18, wherein the molded article comprises at least one surface, and said surface is obtained by chemically modifying a surface thereof after molding.

22. The molded article according to claim 18, wherein the molded article comprises at least one surface, and wherein said surface is provided with, after molding, a membrane containing a copolymer comprising hydrophilic monomer units and hydrophobic monomer units, wherein said monomer units are present in a ratio of hydrophilic monomer units to hydrophobic monomer units of 1:0.01~100.

23. The molded article according to claim 18, wherein the molded article comprises at least one surface, and wherein said surface, after molding, is tightly fixed to a molded article containing a copolymer comprising hydrophilic monomer units and hydrophobic monomer units, wherein said monomer units are present in a ratio of hydrophilic monomer units to hydrophobic monomer units of 1:0.01~100.

24. An ophthalmic material comprising a molded article according to claim 18.

25. A medical material comprising a molded article according to claim 18.

26. An electronic material comprising the molded article according to claim 18.

27. A polydialkylsiloxane/polyamide copolymer comprising a main chain represented by formula (4), a terminal represented by formula (5), and another terminal represented by formula (6):

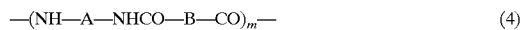
$$\text{—(NH—A—NHCO—B—CO)}_m\text{—} \quad (4)$$

$$\text{—NH—A—NH—X}^2 \quad (5)$$

$$\text{—X}^1 \quad (6)$$

wherein $X^1$ and $X^2$ represent —$COR^4$, —CO—B—$COR^5$, (where $R^4$ represents an organic group having 1 to 7 carbon atom, $R^5$ represents a hydroxyl group, —$OR^6$, or —$NHR^6$ (where $R^6$ represents an organic group having 1 to 7 carbon atoms), and B represents a divalent organic group having 1 to 20 carbon atoms) or a hydrogen atom; A represents —$R^1$(Si($R^2$)($R^3$)—O)$n^1$—Si($R^2$)($R^3$)—$R^1$—(where $R^1$ represents a divalent organic group having 1 to 10 carbon atoms, $R^2$ and $R^3$ are the same or different, each representing an organic group having 1 to 7 carbon atoms, and $n^1$ denotes an integer of 5 to 200) or a divalent organic group having 1 to 20 carbon atoms; B represents a divalent organic group having 1 to 20 carbon atoms; and m denotes an integer of 5 to 200;

wherein the ratio of A groups represented by —$R^1$(Si($R^2$)($R^3$)—O)$n^1$—Si($R^2$)($R^3$)—$R^1$— to A groups represented by divalent organic groups having 1 to 20 carbon atoms, is from 1: 0.01~100, and wherein 10% or less of the $X^1$ and $X^2$ groups are represented by hydrogen atoms.

28. A process for producing a polydialkylsiloxane/polyamide copolymer according to claim 27, wherein a copolymer (A) is first formed, said copolymer (A) comprising a main chain represented by formula (4), a terminal represented by formula (5), and another terminal represented by the formula (6), in which the ratio of A groups represented by —$R^1$—(Si($R^2$)($R^3$)—O)$n^1$—Si($R^2$)($R^3$)—$R^1$ to A groups represented by divalent organic group having 1 to 20 carbon atoms is within the range of 1:0.01~100; said copolymer (A) is subsequently subjected to step (I) or step (II):

step (I): wherein the copolymer (A) is reacted with an acyl chloride having 2 to 8 carbon atoms, to alkylamidate hydrogen atoms present in $X^1$ and $X^2$ of the copolymer (A) so that 10% or less of the $X^1$ and $X^2$ groups are represented by hydrogen atoms;

step (II): wherein the copolymer (A) is reacted with a dicarboxylic acid chloride represented by the formula (3):

$$ClCO\text{—}B\text{—}COCl \quad (3)$$

wherein B represents a divalent organic group having 1 to 20 carbon atoms, to form a reaction product, and subsequently reacting said reaction product with a compound selected from the group consisting of: a monovalent hydroxyl group-containing compound having 1 to 8 carbon atoms, a monovalent amino group-containing compound having 1 to 8 carbon atoms, and mixtures thereof, so that 10% or less of the $X^1$ and $X^2$ groups are represented by hydrogen atoms.

29. A cosmetic composition comprising the polydialkylsiloxane/polyamide copolymer of claim 27.

30. An electronic material comprising the polydialkylsiloxane/polyamide copolymer of claim 27.

31. A molded article obtained by molding a material for molding containing the polydialkylsiloxane/polyamide copolymer according to claim 27.

32. The molded article according to claim 31, wherein said molding is heat-molding, said material comprises a solvent, and wherein said solvent is substantially eliminated as a result of molding.

33. The molded article according to claim 31, which is obtained by, after molding, forming crosslinking by energy beam irradiation.

34. The molded article according to claim 31, wherein the molded article comprises at least one surface, and said article is obtained by chemically modifying a surface thereof after molding.

35. The molded article according to claim 31, wherein the molded article comprises at least one surface, and wherein said surface is provided with, after molding, a membrane containing a copolymer comprising hydrophilic monomer units and hydrophobic monomer units, wherein said monomer units are present in a ratio of hydrophilic monomer units to hydrophobic monomer units of 1:0.01~100.

36. The molded article according to claim 31, wherein the molded article comprises at least one surface, and wherein said surface, after molding, is tightly fixed to a molded article containing a copolymer comprising hydrophilic monomer units and hydrophobic monomer units, wherein said monomer units are present in a ratio of hydrophilic monomer units to hydrophobic monomer units of 1:0.01~100.

37. An ophthalmic material comprising a molded article according to claim 31.

38. A medical material comprising a molded article according to claim 31.

39. An electronic material comprising the molded article according to claim 31.

* * * * *